United States Patent
Iwamiya et al.

(10) Patent No.: US 11,801,267 B2
(45) Date of Patent: Oct. 31, 2023

(54) CARDIAC CELL CULTURE MATERIAL

(71) Applicant: METCELA INC., Yamagata (JP)

(72) Inventors: Takahiro Iwamiya, Tokyo (JP); Katsuhisa Matsuura, Tokyo (JP)

(73) Assignee: METCELA INC., Yamagata (JP)

( * ) Notice: Subject to any disclaimer, the term of this patent is extended or adjusted under 35 U.S.C. 154(b) by 1343 days.

(21) Appl. No.: 16/106,723

(22) Filed: Aug. 21, 2018

(65) Prior Publication Data

US 2018/0369288 A1    Dec. 27, 2018

Related U.S. Application Data

(63) Continuation of application No. 15/401,832, filed on Jan. 9, 2017, now abandoned, which is a continuation-in-part of application No. PCT/JP2015/050028, filed on Jan. 5, 2015.

(30) Foreign Application Priority Data

Jul. 11, 2014  (JP) ................. 2014-142804

(51) Int. Cl.
```
A61K 35/33      (2015.01)
A61K 38/17      (2006.01)
C12N 5/077      (2010.01)
C12N 1/00       (2006.01)
C12N 5/10       (2006.01)
```
(52) U.S. Cl.
CPC .......... *A61K 35/33* (2013.01); *A61K 38/1774* (2013.01); *C12N 1/00* (2013.01); *C12N 5/0656* (2013.01); *C12N 5/0657* (2013.01); *C12N 5/10* (2013.01); *C12N 2501/58* (2013.01); *C12N 2502/1323* (2013.01); *C12N 2502/1329* (2013.01)

(58) Field of Classification Search
CPC .. A61K 35/33; A61K 38/1774; C12N 5/0657; C12N 2501/58; C12N 2502/1329; C12N 2502/1323
See application file for complete search history.

(56) References Cited

U.S. PATENT DOCUMENTS

| | | | |
|---|---|---|---|
| 2006/0193840 | A1 | 8/2006 | Gronthos et al. |
| 2014/0065118 | A1 | 3/2014 | Tedder et al. |

FOREIGN PATENT DOCUMENTS

| | | |
|---|---|---|
| WO | WO-2005/035738 A1 | 4/2005 |
| WO | WO 2014/039804 A1 | 3/2014 |

OTHER PUBLICATIONS

Matsuura Katsuhisa (Biomaterials, 32(30): 7355-7362, 2011) (Year: 2011).*

(Continued)

*Primary Examiner* — Marcia S Noble
*Assistant Examiner* — Lauren K Van Buren
(74) *Attorney, Agent, or Firm* — Alston & Bird LLP

(57) ABSTRACT

The purpose of the present invention is to provide a cardiac cell culture material which specifically acts on cardiac cells. In addition, another purpose of the present invention is to provide artificial organ material obtained by culturing by using said cardiac cell culture material, and a method for producing the same. Thus, provided is a cardiac cell culture, wherein functional cardiac tissue is favorably built by using a cardiac cell culture material containing VCAM-1.

1 Claim, 14 Drawing Sheets

(56) References Cited

OTHER PUBLICATIONS

Kacimi (Circ Res, 82: 576-586, 1998). (Year: 1998).*
Katsuhisa Matsuura et al., Creation of mouse embryonic stem cell-derived cardiac cell sheets, Biomaterials, 2011, vol. 32, pp. 7355-7362.
Katsuhisa Matsurra et al., Regeneration Treatment of Blood Vessel and Myocardium, Biomedicine & Therapeutics, 2009, vol. 43, No. 6, pp. 646-650.
Hidetoshi Masumoto et al., Pluripotent Stem Cell-Engineered Cell Sheets Reassembled with Defined Cardiovascular Populations Ameliorate Reduction in Infarct Heart Function Through Cardiomyocyte-Mediated Neovascularization, Stem Cells, 2012, vol. 30, pp. 1196-1205.
Hideki Uosaki et al., Efficient and Scalable Purification of Cardiomyocytes from Human Embryonic and Induced Pluripotent Stem Cells by VCAMI Surface Expression, PLoS ONE, 2011, vol. 6, No. 8, e23657.
Tatsuya Shimizu et al., Fabrication of Pulsatile Cardiac Tissue Grafts Using a Novel 3-Dimensional Cell Sheet Manipulation Technique and Temperature-Responsive Cell Culture Surfaces, Circulation Research, 2002;90:e40.
Sachiko Sekiya et al., Bioengineered cardiac cell sheet grafts have intrinsic angiogenic potential, Biochemical and Biophysical Research Communications, 2006, vol. 341, pp. 573-582.
Tatsuya Shimizu et al., Cell sheet engineering for myocardial tissue reconstruction, Biomaterials, 2003, vol. 24, pp. 2309-2316.
Anne M. Deschamps et al., Disruptions and Detours in the Myocardial Matrix Highway and Heart Failure, Current Heart Failure Reports,2005, vol. 2, pp. 10-17.
Lia Kwee et al., Defective development of the embryonic and extraembryonic circulatory systems in vascular cell adhesion molecule (VCAM-1) deficient mice, Development (Cambridge, England), 1995, vol. 121, pp. 489-503.
Joy T. Yang et al., Cell adhesion events mediated by a4 integrins are essential in placental and cardiac development, Development (Cambridge, England), 1995, vol. 121, pp. 549-560.
Masaki Ieda et al., Cardiac Fibroblasts Regulate Myocardial Proliferation through b1 Integrin Signaling, Development Cell, 2009, vol. 16, pp. 233-244.
Le, Tyl et al. "Cardiac Progenitor Cells for Heart Repair." Official journal of the Cell Death Differentiation Association; Cell Death Discovery (2016) vol. 2, 16052, 4 pages.
Matsuura, Katsuhisa et al. "Transplantation of cardiac progenitor cells ameliorates cardiac dysfunction after myocardial infarction in mice." The Journal of Clinical Investigation, vol. 119, No. 8, Aug. 2009, 14 pages.
Extended European Search Report for European Patent Application No. 15819754.1 dated Feb. 7, 2018, 10 pages.
Iwamiya, Takahiro et al. "Cardiac fibroblast-derived VCAM-1 enhances cardiomyocyte proliferation for fabrication of biogengineered cardiac tissue." Regenerative Therapy, vol. 4 (2016), pp. 92-102.
International Search Report and Written Opinion from International Application No. PCT/JP2015/050028, dated Mar. 24, 2015, 8 pages.
Office Action from corresponding Japanese Patent Application No. 2015-138613, dated Jul. 25, 2017, 13 pages.
Haraguchi, Yuji et al.; "Electrical Coupling of Cardiomyocite Sheets Occurs Rapidly Via Functional Gap Junction Formation"; Biomaterials 27 (2006); pp. 4765-4774.
Zeisberg, Elisabeth et al.; Fibroblasts in Kidney Fibrosis Emerge Via Endothelial-to-Mesenchymal Transition; J Am Soc Nephrol 19:2282-2287, 2008.
Bax, Noortje et al; "In Vitro Epithlial-to-Mesenchymal Transformation in Human Adult Epicardial Cells is Regulated by TGF β-Signaling and WT1"; Basic Res. Cardiol (2011) vol. 106, pp. 829-847.
Chen et al., Hypertension, 2005, vol. 46, p. 622-627.
Ruiz-Villalba et al., PLOS, Jan. 2013, vol. 8, Issue 1, e53694, p. 1-12.
Merriam-Webster online dictionary, definition of "cardiac", downloaded on May 16, 2018.
Notification of Decision to Grant a Patent for Japanese Application No. 2015-138613 dated Oct. 11, 2017.

* cited by examiner

CARDIAC CELL CULTURE MATERIAL

CROSS-REFERENCE TO RELATED APPLICATION

This is a continuation of U.S. patent application Ser. No. 15/401,832, filed on Jan. 9, 2017, which was a continuation-in-part of International Application PCT/JP2015/050028, which was filed on Jan. 5, 2015, and designated the U.S., and claims priority from Japanese Patent Application 2014-142804, which was filed on Jul. 11, 2014, the entire contents of each of which are incorporated herein by reference.

TECHNICAL FIELD

The present invention relates to a cardiac cell culture material and a cell culture substrate on which a wall surface and/or a bottom surface of the culture substrate having the wall surface and/or the bottom surface are coated with the cardiac cell culture material. In addition, the present invention relates to an artificial organ material obtained by culturing a cardiac cell by using the cardiac cell culture material, and a method for producing the same.

BACKGROUND ART

Fibroblasts exist in almost all of vertebrate, and when tissue is injured by trauma and ischemia, the injured area is replaced with fibrous tissue in accordance with fibroblasts proliferation and the abundant extracellular matrix deposition. Likewise, in a variety of heart disease such as myocardial infarction and cardiomyopathies, a lot of cardiomyocytes were lost and also fibrous tissue replaces that area, which leads to cardiac remodeling and heart failure accompanied with excess hemodynamics stress and neurohumoral stimulation. Although neurohumoral factors such as angiotensin II and endothelin-1 are well known to contribute to promote the cardiac remodeling via blood pressure elevation, cardiomyocyte apoptosis and local inflammation, cardiac fibroblasts have been reported to secrete those factors. Cardiac fibroblasts are also known to play a critical role in heart developments. Interconnected cellular processes in a cardiac fibroblast form a network of collagen, fibroblasts and myocytes. Although cardiomyocyte proliferation is indispensable process of formation of thick ventricular wall and embryonic cardiac fibroblasts have also been reported to promote myocardial mitotic activity through β-1 integrin signaling. The cardiac fibroblasts dominant causative substance has been unclear. Herein cardiac fibroblasts multifariously act on heart development and pathogenesis and the importance of understanding of mutual interaction and underlying mechanisms between cardiomyocytes and cardiac fibroblasts have been widely recognized. However the uncertain properties of cardiac fibroblasts were the bottleneck for it and it is required to reveal functional and molecular biological characteristics of cardiac fibroblasts.

Heart tissue engineering is promising methods for not only regenerative medicine, but also tissue models. Among cardiac tissue engineering methods, cell sheet-based cardiac tissue using temperature responsive culture dishes have been developed. Previously, it was reported that layering of cardiac cell sheets containing neonatal rats-derived cardiomyocytes, fibroblasts and endothelial cells on the various types of vascular bed enabled to fabricate three-dimensional vascularized viable cardiac tissue (Non patent documents 1 to 3). Since cell sheet-based tissue engineering does not need any scaffold, it requires some amounts of extracellular matrices to construct cell sheets. Consistent with the evidences that left ventricle is mainly composed of fibroblasts and cardiomyocytes, some amounts of fibroblast are indispensable to fabricate cardiac cell sheets when using purified embryonic stem cell-derived cardiomyocytes (Non patent document 4). Since recent reports have suggested that cell-cell interaction between cardiomyocytes and non-myocytes is important for heart physiology and pathogenesis (Non patent document 5), fibroblasts function might also affect the function of the engineered cardiac tissue and it might be prerequisite to select the suitable fibroblasts to fabricate the cardiac tissue in vitro for tissue models. However it remains unclear whether cardiac fibroblasts have the specific function for cardiomyocytes compared with other types of fibroblasts and the related molecular mechanisms.

As mentioned above, since the cardiac fibroblasts play an important role in heart developments, and the onset or cure of heart diseases, it is required to separate cardiac fibroblasts that specifically act on cardiac cells such as cardiomyocytes from other fibroblasts, and to sample the cardiac fibroblasts. According to the recent studies, it has been revealed that fibroblasts, which were previously considered as a uniform cell type, have a great variety of phenotypes, and that the phenotypes differ depending on a load state of existing organs, tissues or cells.

However, the function of fibroblasts is not clearly known, and fibroblasts are only cells morphologically classified. Therefore, among fibroblasts, it is difficult to select only one type thereof having a specific function.

Meanwhile, with respect to vascular cell adhesion molecule-1 (VCAM-1, CD106) and α4 integrin, Kwee, et al. reported that VCAM-1 was expressed on embryonic day 11.5 at epicardium, cardiomyocytes, ventricular septum, and the like. It was also reported that, although the expression of α4 integrin was recognized at similar areas as those of VCAM-1, α4 integrin was not expressed in ventricular septum (Non patent document 6). Moreover, it was reported that, on embryonic day 11.5, there are embryonic death resulting from inhibition of formation of the placenta, and deformity due to decrease in dense layers of ventricular myocardium and ventricular septum in an embryo that is defective in VCAM-1. Yang, et al. also reported an epicardium defect in α4 integrin null embryo of embryonic day 11.5 (Non patent document 7). Accordingly, it is considered that VCAM-1 and α4 integrin mainly contribute to formation of cardiac cells and epicardium in the embryonic stage.

CITATION LIST

Non-Patent Document

Non-Patent Document 1: Shimizu T, et al., Fabrication of pulsatile cardiac tissue grafts using a novel 3-dimensional cell sheet manipulation technique and temperature-responsive cell culture surfaces. Circulation research. 2002; 90:e40

Non-Patent Document 2: Sekiya S, et al., Bioengineered cardiac cell sheet grafts have intrinsic angiogenic potential. Biochemical and biophysical research communications. 2006; 341:573-582

Non-Patent Document 3: Shimizu T, et al., Cell sheet engineering for myocardial tissue reconstruction. Biomaterials. 2003; 24:2309-2316

Non-Patent Document 4: Matsuura K, et al., Hagiwara N, Zandstra P W, Okano T. Creation of mouse embryonic stem cell-derived cardiac cell sheets. Biomaterials. 2011; 32:7355-7362

Non-Patent Document 5: Deschamps A M, et al., Disruptions and detours in the myocardial matrix highway and heart failure. Current heart failure reports. 2005; 2:10-17

Non-Patent Document 6: Kwee L, et al., Defective development of the embryonic and extraembryonic circulatory systems in vascular cell adhesion molecule (vcam-1) deficient mice. Development (Cambridge, England). 1995; 121: 489-503

Non-Patent Document 7: Yang J T, et al., Cell adhesion events mediated by alpha 4 integrins are essential in placental and cardiac development. Development (Cambridge, England). 1995; 121:549-560

SUMMARY OF INVENTION

Technical Problem

One purpose of the present invention is to provide a cardiac cell culture material which specifically acts on cardiac cells, and to provide a cell culture substrate on which a wall surface and/or a bottom surface of the culture substrate having the wall surface and/or the bottom surface are coated with the cardiac cell culture material. In addition, another purpose of the present invention is to provide an artificial organ material obtained by culturing a cardiac cell by using the cardiac cell culture material, and a method for producing the same.

Solution to Problem

It has been made clear that, in cardiac cell culturing, a functional cardiac tissue is well constructed by using a cardiac cell culture material containing VCAM-1 protein. Therefore, the cardiac cell culture material is coated on a wall surface and/or a bottom surface of a culture substrate having the wall surface and/or the bottom surface, and can be used as a cell culture substrate. A cardiac cell cultured by using the cardiac cell culture material can be used as an artificial organ material.

Namely, the present invention includes followings.

[1] A cardiac cell culture material comprising VCAM-1 protein.

[2] The cardiac cell culture material according to [1], wherein the VCAM-1 protein is a VCAM-1 separated and purified from an animal material, a VCAM-1 recombinant protein, or a cell expressing VCAM-1 protein.

[3] The cardiac culture material according to [1] or [2] used for culturing to construct a cardiac tissue.

[4] The cardiac cell culture material according to [2] or [3], wherein the cell expressing VCAM-1 protein is a fibroblast expressing VCAM-1 protein.

[5] The cardiac cell culture material according to [4], wherein the fibroblast is a cardiac-derived fibroblast.

[6] The cardiac cell culture material according to [4] or [5], wherein the fibroblast is an epicardial-derived fibroblast.

[7] A cell culture substrate, wherein a wall surface and/or a bottom surface of the culture substrate having the wall surface and/or the bottom surface are coated with the cardiac cell culture material according to [1]-[6].

[8] An artificial organ material obtained by co-culturing a cardiac cell with the cardiac cell culture material according to [1]-[6].

[9] A method of producing an artificial organ material comprising a step of co-culturing a cardiac cell with the cardiac cell culture material according to [1]-[6].

[10] A reagent for screening a cardiac cell culture material containing an anti-VCAM-1 antibody.

[11] A cardiac-derived fibroblast expressing VCAM-1 protein.

[12] A method of producing the artificial organ material according to [9] further including a step of separating and collecting a cultured cell from a culture substrate.

[13] A method of producing the artificial organ material according to [12], wherein the culture substrate is a temperature responsive culture dish, and wherein the separation is performed by temperature change.

[14] A method of producing the artificial organ material according to [9] further including the step of agglomerating the co-cultured material by using scaffold having thickness in a certain extent.

[15] A method of producing the artificial organ produced from the artificial organ material according to [9] comprising step of using a 3D printer.

Advantageous Effects of Invention

A functional cardiac cell which can be used in a regenerative medicine and an organizational model can be constructed by culturing a cardiac cell by using the cardiac cell culture material of the present invention. The cardiac cell culture material can be coated on a wall surface and/or a bottom surface of a culture substrate having the wall surface and/or the bottom surface, which can be used as a cell culture substrate. Further, a cardiac cell or a cardiac tissue obtained by culturing can be used as an artificial organ material.

DESCRIPTION OF EMBODIMENTS

Figure 1:
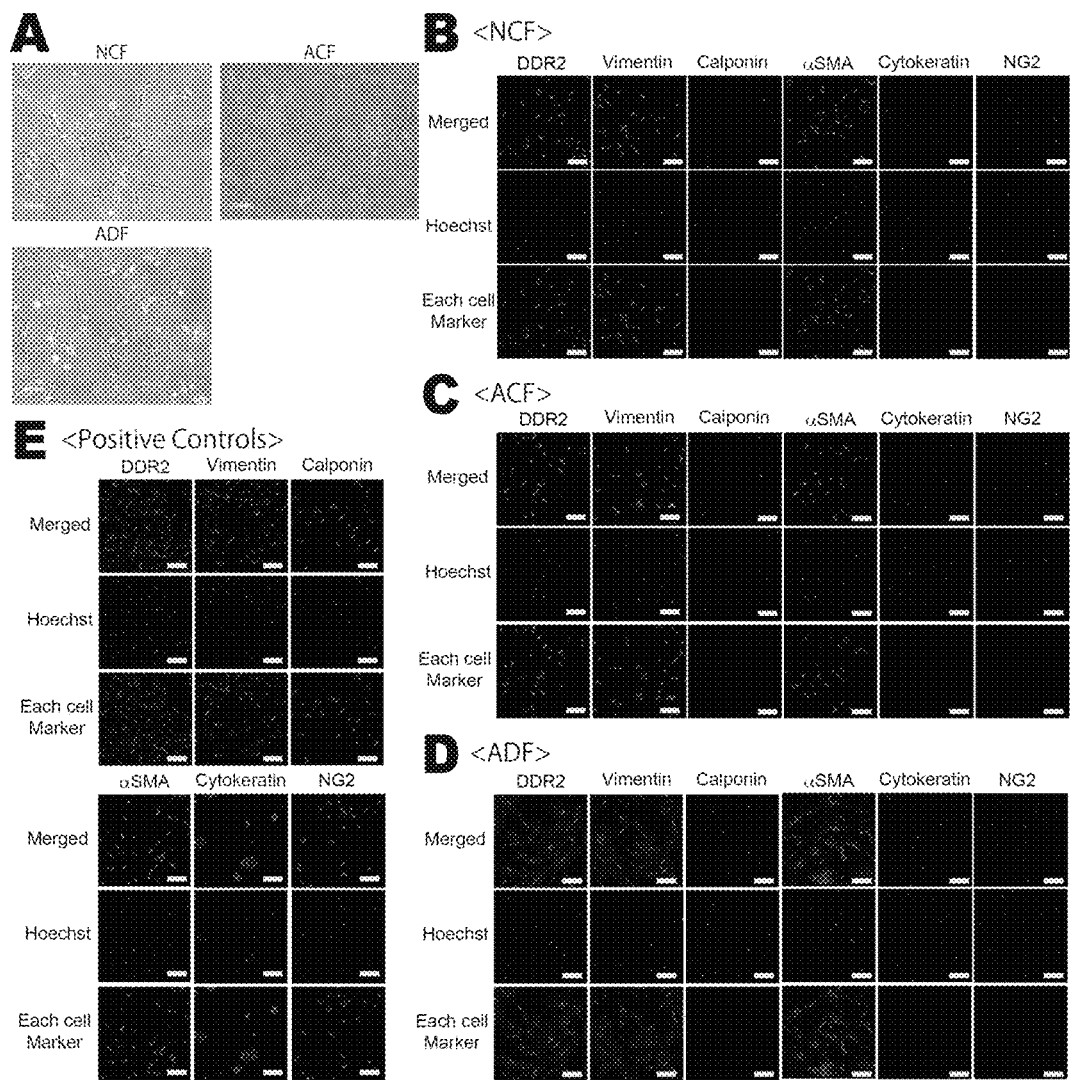
[FIG. 1] A microscopic observation of NCF, ACF and ADF (photographs). (A) Bright field microscope images of each fibroblast. (B-E) Representative Figures of DDR2, vimentin and αSMA expression (Most of the fibroblasts were not expressing calponin, cytokeratin 11 or NG 2).

The present embodiment relates to a cardiac cell culture material containing VCAM-1. In the present embodiments, the "cardiac cell culture material" may be any material that is used when culturing a cardiac cell. For example, the material includes but is not limited to a reagent such as a protein, and a peptide, etc. to be added to a culture medium, and a material, etc. for coating a bottom surface or a wall surface of a culture substrate of a culture vessel, etc. such as a petri dish and a flask, and the like. Examples of these cell culture substrate, in which a wall surface and/or a bottom surface of the culture substrate having the wall surface and/or the bottom surface are coated with the cardiac cell culture material include microcarrier, and cell culture bag, etc.

VCAM-1 (vascular cell adhesion molecule-1) is a known protein as a cell adhesion molecule that expresses in a vascular endothelial cell, and the like. For example, in the case of humans, VCAM-1 includes but not limited to a protein encoded by a gene described in accession number NM_001078, etc. of NCBI (National Center for Biotechnology Information), and also includes an isoform obtained by alternative splicing. The VCAM-1 protein in the present embodiment includes VCAM-1 which is expressing on a cell surface, a soluble VCAM-1, various mutants one or a plurality of, for example, 1-20, 1-15, 1-10 or 1-5 of amino acids of which have been deleted from, substituted from, or added to an amino acid of VCAM-1 protein and having the same activity as VCAM-1 protein. A VCAM-1 protein in an animal material which has been separated and purified by a well-known method and a recombinant protein may be used as the VCAM-1 in the present embodiment. For example, the animal material includes but is not limited to humans; experimental animals such as mice, rats, guinea pigs, hamsters, pigs, monkeys and rabbits; and bacteria such as $E.\ coli$, etc. A commercially available recombinant protein may be also used.

Moreover, a cell that is expressing VCAM-1 may be used as VCAM-1 of the present embodiment. In order to screen a cell that is expressing VCAM-1, a publicly known cell sorting method may be used. For example, the cell sorting method includes but not limited to flow cytometry using an anti-VCAM-1 antibody, magnetic bead method, affinity column method, and panning method.

Anti-VCAM-1 antibodies are not particularly limited. Commercially available anti-VCAM-1 antibodies may be used, and a product produced by a known method by using VCAM-1 as an antigen may be also used. Moreover, as far as the cells that are expressing VCAM-1 may be screened, either monoclonal antibody or polyclonal antibody may be used; however, it is preferred to use monoclonal antibody from the viewpoint of specificity.

Namely, the methods of screening the cardiac cell culture materials of the present embodiment include, a step of preparing cells, a step of performing cell sorting to the cells by using a VCAM-1 antibody, and a step of collecting only cells that have been judged to be expressing VCAM-1 as a result of the cell sorting.

As the cell that is expressing VCAM-1, the types are not limited as far as VCAM-1 is expressed. However, it is preferred to use fibroblasts. The fibroblasts include all the cells that will ultimately become fibroblasts or myofibroblasts. Namely, the scope of fibroblasts of the present embodiment includes the cells that are in the middle of differentiation or a maturation stage and cannot be identified as fibroblasts or myofibroblasts at that time as far as the cells will ultimately become fibroblasts or myofibroblasts. Moreover, the scope of fibroblasts of the present embodiment includes the cells that are not called as fibroblast, such as stromal cells, interstitial cells, progenitor cells, precursor cells, stem cells, or the like, as far as the cells have the same functions and activities as fibroblasts and express VCAM-1.

Derivation of fibroblasts is not limited. Pluripotent stem cells such as ES cells, iPS cells and muse cells, and adult stem cells such as mesenchymal stem cells may be differentiated and used, and primary cells taken from animals may be used, and established cells may be used. However, cardiac-derived fibroblasts are preferably used, and among them, epicardium-derived fibroblasts are in particular preferred to be used. In a case where established cells are used, processing of cell sorting may be omitted by selecting the cells that are known to express VCAM-1. The animals from which fibroblasts are derived may be appropriately selected in accordance with the animals from which the cells to be co-cultured are derived. The animals, for example, include humans; experimental animals such as mice, rats, guinea pigs, hamsters, pigs, monkeys and rabbits; pet animals such as dogs, cats and birds; and livestock such as cattle, horses, sheep and goats. In a case where fibroblasts are taken from animals, the fibroblasts may be of at any time of the animals such as fetus, neonate, infant, adult, and there is no limit.

The cardiac cell culture material of the present embodiment may be a composition containing physiological saline, cell culture solution, or cell preservation solution, etc. for maintenance or preservation of VCAM-1 protein or cells that are expressing VCAM-1 protein. There is no limit on the contents contained in the composition as far as the contents do not impair the function of VCAM-1. Moreover, the state of the cardiac cell culture material of the present embodiment may be liquid, gel-like, freezed, or freeze-dried, and the state thereof is not limited.

Further, the cardiac cell culture material may include fibroblasts regardless of presence or absence of VCAM-1 protein. The fibroblasts include all the cells that will ultimately become fibroblasts or myofibroblasts. Namely, even if the cells are in the middle of differentiation or a maturation stage and cannot be identified as fibroblasts or myofibroblasts at that time, if the cells are those that will ultimately become fibroblasts or myofibroblasts, the cells may be used without limit. Among them, fibroblasts that are expressing CD31 (vascular endothelial cell marker) are preferred. When fibroblasts that are expressing VCAM-1 protein are used as VCAM-1 protein, the ratio of VCAM-1 protein expressing cells (cell number): CD31 expressing cells (cell number) are preferably 5:5-9:1, more preferably 5:5-8.2, even more preferably 6:4-8.2, and may be 7:3-8:2.

The present embodiment relates to an artificial organ material in which the ratio of cardiac fibroblasts expressing VCAM-1 to all the cells is 50% or higher. The ratio of the cardiac fibroblasts is 50% or higher, and preferably 60% or higher, and more preferably 70% or higher, and even more preferably 80% or higher, and most preferably 90% or higher. The artificial organ material may be obtained by co-culturing cardiac fibroblasts that express VCAM-1 with cardiomyocytes, and the ratio of the cardiac fibroblasts at the start of co-culturing is normally 3% or higher, preferably 4% or higher, more preferably 6% or higher, and even more preferably 8% or higher, and most preferably 9% or higher. Meanwhile, the ratio of the cardiac fibroblasts at the start of co-culturing is preferably 30% or lower, preferably 20% or lower, and most preferably 20%. The present invention also relates to an artificial organ material obtained by culturing a cardiac cell with the above-mentioned cardiac cell culture material, or a method for producing the same. Namely, the cardiac cell culture material of the present embodiment can construct a functional cardiac tissue that can be used in a regenerative medicine and organizational model by culturing with a cardiac cell. The cardiac tissue can be used as an artificial organ material. The artificial organ material can be of any form. For example, it can be adhered to a damaged part of organs such as heart in the form of sheet. Therefore, one embodiment is a method for curing heart diseases by attaching the sheet to a damaged part of the heart. The artificial organ material can be also transplanted to a defect site of an organ after it is laminated or it is agglomerated by using scaffold, which has thickness in a certain extent. The material of the scaffold includes but not limited to hydroxyapatite, atelocollagen, and gel. Further, the artificial organ material can be used for cell transplantation, academic research, etc. as it is in the state of the culture cell, without making it to be a particular form. Furthermore, an artificial organ can be produced from the artificial organ material by using a 3D printer. The produced artificial organ not only can be used for transplantation but also can be widely used for safety pharmacology test and preclinical research, etc.

In the present embodiment, "constructing a cardiac tissue" means constructing a tissue having at least one of the cardiac functions such as promoting division of cardiac cells, and providing uniform beating throughout a whole tissue, which can be used for regenerative medicine and a tissue model. The cardiac functions include all the known cardiac functions such as autonomous pulsating ability, contraction and relaxation ability, impulse conduction ability, and hormone secretion ability, etc. The cardiac functions are not limited to functions which only the heart has. For example, a muscle cell also has the contraction and relaxation ability. However, even if other cells have an equivalent function, it does not affect the definition of the cardiac functions of the present embodiment. Further, with respect to the cardiac functions, there is no limit on highness and lowness of the functions as long as they are suitable for use purpose of a cardiac tissue. For example, for the purpose of producing an artificial heart, it is required to have a contraction and relaxation ability to the extent that it can pump out blood thought out the body; however, for the purpose of academic research, etc. of contraction and relaxation ability in vitro, it is satisfied if contraction and relaxation ability is detected by some means.

In the artificial organ material, or the method to produce the same of the present embodiment, cardiac cells to be used include all the cells that constitute the heart such as cardiomyocytes, smooth muscle cells, pacemaker cells and vascular endothelial cells. The derivation of the cardiac cells can be appropriately set in accordance with the purpose of use as an artificial organ material. For example, for the purpose of transplantation to humans, human-derived cardiac cells may be used, and for the purpose of constructing a tissue model in a mouse experiment, mouse-derived cardiac cells may be used. Furthermore, a cardiac cell of any period from fetus, newborn, pediatric and adult can be used, and there is no limit on the period. The cardiac cell of the present embodiment is preferred to be produced from pluripotent stem cells such as ES cells, iPS cells, and muse cells, and adult stem cells such as mesenchymal stem cells.

The "culturing" of the present embodiment can be carried out by a publicly known cell culturing method, and there is no limit on the condition of the culturing as long as a cardiac cell culture material and a cardiac cell are present in a culture vessel, or are immersed in the same culture medium. In a case where the cardiac cell culture material are cells which are expressing VCAM-1 protein, the mixing percentage of the cells (cell number) that are expressing VCAM-1 to cardiac cells are preferably 3-20%, more preferably 6-18% and most preferably 9-16%.

In the present embodiment, a culture liquid used for the culturing can be appropriately set in accordance with a kind of cell to be cultured. For example, DMEM, α-MEM, RPMI-1640, and the like may be used. Nutritional substances such as FCS and FBS and antibiotics may be added to the culture liquid. Growth factor and cytokines such as fibroblast growth factors (FGF) may also be added to the culture liquid.

With respect to the cultivation period, the number of days until the desired cell number and/or function are obtained may be appropriately set. For example, the periods include 1 day, 2 days, 3 days, 4 days, 5 days, 6 days, 7 days, 8 days, 9 days, 10 days, 11 days, 12 days, 13 days, 14 days, 1 month, 2 months, 3 months, 4 months, 5 months, and 6 months. The cultivation temperature may be appropriately set in accordance with the kinds of cells to be cultured. For example, the temperature may be 10-60° C., preferably 20-50° C., and more preferably 30-40° C.

The production method of the present embodiment may further include the step of collecting cultured cells. The "cultured cells" may include both fibroblasts and cardiac cells, and may only include the cardiac cells. With respect to the step to collect a cell, the cell may be separated and collected by using proteases such as trypsin. However, it is preferred that cell is separated and collected by the change in temperature by using a temperature responsive culture dish capable of separating a cell while retaining an extracellular matrix, etc.

EXAMPLES

The present invention is further described below in detail with reference to the following examples; however, it should be construed that the invention is no way limited to those examples.

Example 1

Materials and Methods
<Animals and Reagents>

Wild-type C57BL/6 mice were purchased from Japan SLC (Shizuoka, Japan). B6 Cg-Tg (CAG-DsRed*MST) 1Nagy/J mice were purchased from The Jackson Laboratory (Bar Harbor, Me.). All the experimental protocols were approved by the Institutional Animal Care and Use Committee of Tokyo Women's Medical University. The following antibodies were used for immune cytochemistry, western blot and flow cytometric analysis (FACS): rabbit polyclonal anti-discoidindomein receptor tyrosine kinase 2 (DDR2) (GeneTex, Irvine, Calif.); guinea pig monoclonal anti-vimentin (Progen, Heidelberg, Germany); mouse monoclonal anti-NG2 (Millipore, Temecula, Calif.); Rabbit polyclonal anti-alpha smooth muscle actin (Abcam, Cambridge, UK); mouse monoclonal anti-cardiac troponin T (cTnT) (Thermo Scientific, Rockford, Ill.); mouse monoclonal anti-cytokeratin11 (EXBIO, NadSafinou, CZ); rabbit polyclonal anti-Ki67 (Abcam, Cambridge, UK); rabbit polyclonal anti-Histon H3 (phosphor S10) (Abcam, Cambridge, UK); rat monoclonal anti-integrin $\alpha4/\beta1$ (Abcam, Cambridge, UK); recombinant mouse VCAM-1/CD106 Fc chimera (R&D systems, Minneapolis, Minn.). Unless otherwise specified, all reagents were purchased from Sigma-Aldrich. Secondary antibodies were purchased from Jackson ImmunoResearch Laboratories (West Grove, Pa.).

<Mouse ES Cell Cultures>

The maintenance of mESC expressing the neomycin phosphotransferase gene under the control of the $\alpha$-myosin heavy chain promoter and cardiomyocyte differentiation and purification were described previous report (Matsuura K, et al. Biomaterials. 2011; 32:7355-7362). Briefly, for cardiac induction and cardiomyocyte purification, trypsinized ES cells were seeded at $5\times10^4$ cells/mL (total, 125 mL/flask) into spinner flasks (Integra Biosciences, Zizers, Switzerland) and cultured with DMEM supplemented with 10% FBS for 10 days, then these differentiated cells were treated with neomycin for further 8 days.

<Fibroblast Isolations>

Fibroblasts were obtained from Wild-type C57BL/6 mice (Neonatal, 1 day; Adult, 10-12 weeks).

Neonatal cardiac fibroblasts (NCFs) were obtained from hearts of neonatal mice (1 day of age) as described previous report (Matsuura K, et al., Biomaterials. 2011; 32: 7355-7362). NCFs from passage 3 were used for the experiments.

Adult cardiac fibroblasts (ACFs) were obtained from hearts of adult mice (10-12 weeks) using the explant culture method as follow. First hearts were washed with PBS(−) and cut into circa 5 mm$^2$ species. These species were covered with sterilized cover glasses and cultured with DMEM supplemented with 10% FBS on 10 cm culture dishes. 2 weeks after starting culture, cells were dissociated with 0.25% Trypsin/EDTA and subcultured to other 10 cm dishes. ACFs from passage 3 were used for the experiments.

Adult dermal fibroblasts (ADFs) were obtained from dorsal dermal tissue of adult mice (10-12 weeks). First harvested dermal tissues were treated with Dispase I [1000 U/mL] (Eidea inc.) over night at 4° C. Next, the tissues were cut into circa 1 mm$^2$ species. These species were covered with sterilized cover glasses and cultured with DMEM supplemented with 10% FBS on 10 cm culture dishes. 2 weeks after starting culture, cells were dissociated with 0.25% Trypsin/EDTA and subcultured to another 10 cm dishes. ADFs from passage 3 were used for the experiments.

In some experiments, NCFs and ADFs were isolated from B6.Cg-Tg (CAG-DsRed*MST) 1Nagy/J mice (Neonatal: 1 day, Adult: 10 weeks) with the same methods as described above.

<Cell Sheet Preparation>

Before seeding cells, the surface of temperature-responsive culture dishes (UpCell; CellSeed inc.) was coated with FBS for 2 h. mESC-derived cardiomyocytes were co-cultured with each type of fibroblasts at the ratio of 8:2 with DMEM supplemented with 10% FBS ($3.2\times10^5$ cells/cm$^2$). After 5 days of culture, the cells were incubated at 20° C. for detaching cell sheets. Bright field images of samples were obtained by a Nikon ECLIPSE Ti (Nikon, Tokyo, Japan).

<Electrophysiological Analysis>

The electrical activities of the cardiomyocyte sheets were obtained from the extracellular potentials measured by a multi-electrode array (MED) system (Alpha MED Sciences inc.) as described previous report (Matsuura K, et al., Biomaterials. 2011; 32:7355-7362).

<Immunocytochemistry>

Cells were fixed with 4% paraformaldehyde and subjected to immunostaining as described previous report (Matsuura K, et al., Biomaterials. 2011; 32:7355-7362). Images of the stained samples were obtained by an ImageXpress Ultra Confocal High Content Screening System (Molecular Devices, CA, USA). Image analysis data was obtained by a MetaExpress software (Molecular Devices inc.).

<FACS Analysis>

Incubating cells ($5\times10^5$ cells) were stained with BrdU at a final concentration of 10 μM in cell culture medium. BrdU staining for a FACS analysis was performed as described in a BrdU Flow Kits Instruction Manual (BD Pharmingen, Franklin Lakes, N.J.). Briefly, cells were fixed and permeabilized with BD Cytofix/Cytoperm Buffer, then exposed incorporated BrdU with DNase. BrdU staining was performed with APC-anti-BrdU antibody (BD Pharmingen, Franklin Lakes, N.J.). Samples were analysed with a Gallios (Beckman Coulter, Brea, Calif.). The following reagents were used for the analysis: BD Cytofix/Cytoperm Buffer (BD Pharmingen, Franklin Lakes, N.J.); BD Perm/Wash Buffer (10×) (BD Pharmingen, Franklin Lakes, N.J.); BD Cytoperm Plus Buffer (10×) (BD Pharmingen, Franklin Lakes, N.J.); BrdU (10 mg/mL) (BD Pharmingen, Franklin Lakes, N.J.); DNase (BD Pharmingen, Franklin Lakes, N.J.).

<Time-Laps Photography>

Samples were observed five days in 5% $CO_2$ at 37° C. with a BZ-9000 Fluorescence Microscope (Keyence, Osaka, Japan).

<RNA Extraction and Comprehensive Genetic Analysis>

Total RNA was extracted using TRIzol reagent (Invitrogen, Carlsbad, Calif.) according to the manufacturer's instructions. Total RNA was further purified using the Qiagen RNeasy Mini Kit (QIAGEN, Valencia, Calif.) according to the manufacturer's instructions.

RNA quantity and quality were determined using a Nanodrop ND-1000 spectrophotometer (Thermo Fisher Scientific Inc., Waltham, Mass.) and an Agilent Bioanalyzer (Agilent Technologies, Palo Alto, Calif.), as recommended.

For cRNA amplification and labeling, total RNA was amplified and labeled with Cyanine 3 (Cy3) using Agilent Low Input Quick Amp Labeling Kit, one-color (Agilent Technologies, Palo Alto, Calif.) following the manufacturer's instructions. Briefly, 100 ng of total RNA was reversed transcribed to double-strand cDNA using a poly dT-T7 promoter primer. Primer, template RNA and quality-control transcripts of known concentration and quality were first denatured at 65° C. for 10 min and incubated for 2 hours at 40° C. with 5× first strand Buffer, 0.1 M DTT, 10 mM dNTP mix, and Affinity Script RNase Block Mix. The AffinityScript enzyme was inactivated at 70° C. for 15 min.

cDNA products were then used as templates for in vitro transcription to generate fluorescent cRNA. cDNA products were mixed with a transcription master mix in the presence of T7 RNA polymerase and Cy3 labeled-CTP and incubated at 40° C. for 2 hours. Labeled cRNAs were purified using QIAGEN's RNeasy mini spin columns and eluted in 30 μl of nuclease-free water. After amplification and labeling, cRNA quantity and cyanine incorporation were determined using a Nanodrop ND-1000 spectrophotometer and an Agilent Bioanalyzer.

For Sample hybridization, 1.65 μg of Cy3 labeled cRNA were fragmented, and hybridized at 65° C. for 17 hours to an Agilent Mouse GE 4x44Kv2 Microarray (Design ID: 026655). After washing, microarrays were scanned using an Agilent DNA microarray scanner.

For data analysis of microarray, intensity values of each scanned feature were quantified using Agilent feature extraction software version 10.7.3.1, which performs background subtractions.

We only used features that were flagged as no errors (present flags) and excluded features that were not positive, not significant, not uniform, not above background, saturated, and population outliers (marginal and absent flags). Normalization was performed using Agilent GeneSpring GX version 11.0.2. (per chip: normalization to 75 percentile shift; per gene: normalization to median of all samples). There are total of 39,429 probes on Agilent Mouse GE 4x44Kv2 Microarray (Design ID: 026655) without control probes.

The altered transcripts were quantified using the comparative method. We applied 2-fold change in signal intensity to identify the significant differences of gene expression in this study.

<Quantitative Real-Time PCR Analysis>

Complementary DNA was generated from total RNA with High Capacity cDNA Reverse Transcription Kit (Applied biosystems). As the PCR-related primers, VCAM-1 Gene Express Assays (life Technology) was used.

Each RT-PCR included 10 minutes at 25° C., 120 minutes at 37° C., and 5 seconds at 85° C. with iCycler (BIO-RAD). cDNA template (1 μg) was used from each sample. TaqMan probe real-time PCR studies were performed with TaqMan Gene Expression Assays (Applied biosystems). All experiments were conducted in triplicate. Samples were cycled 40 times with an 7300 Real Time PCR System (Applied Biosystems) as follows: 2 minutes at 50° C. and 10 minutes at 95° C., followed by 40 cycles of 15 seconds at 95° C. and 1 minute at 60° C. Relative quantification was calculated according to the $\Delta\Delta CT$ method for quantitative real-time PCR using a Gap DH gene as endogenous control.

<Western Blotting>

NCFs or ADFs were lysed in Laemmli sample buffer (BIO-RAD, CA, USA), protease inhibitor (Boehringer Mannheim, Indianapolis, Ind.) and 2-mercaptoethanol (Wako Pure Chemical Industries, Japan). The samples were separated on a 4% to 12% Bis-Tris Gels (Life Technologies, MD, United States), electrotransferred to a iBlot Transfer Stack, nitrocellulose, regular-size (Life technologies, MD, United States) with iBlot 7-Minute Blotting System (Life technologies, MD, United States), and processed for chemiluminescence analysis with Amersham ECL Prime Western Blotting Detection Reagent (GE Healthcare, PA, United States). Band intensity was analyzed using LAS4000 (Fujifilm, Tokyo, Japan) and NIH image software (version 1.46r). The following cell transient overexpression lysates were used for positive controls: K562 (Human erythromyeloblastoid leukemia cell line) for Col11a1 (Abcam, CB, UK); Sol8 (SantaCruz, Calif., USA) for Vcam-1; ITGB1 293T for β1/CD29 (Abnova, Taipei, Taiwan); Jurkat Whole Cell Lysate for integrin α4β1 (SantaCruz, Calif., USA).

<Neutralizing Antibodies Assay>

The following antibodies and culture dishes were used for neutralizing antibody assay: anti-VCAM-1 (LifeSpan Biosciences, Seattle, Wash.); goat IgG isotype control (LifeSpan Biosciences, Seattle, Wash.). Cell Culture Inserts for 24-well plates. 0.4 μm pores, Translucent, High Density PET Membrane (BD Pharmingen,Franklin Lakes, N.J.).

After the pretreatment with the antibodies at 10 μg/mL for 30 min, fibroblasts were seeded onto the upper layer of insert culture dishes ($2.4 \times 10^5$ cells). mESC-derived cardiomyocytes were seeded onto the below layer ($4.8 \times 10^5$ cells). The culture medium with the antibody at 10 μg/mL was changed every day until 5 days.

<Statistical Analysis>

All data were presented as the mean±SD. The significance of the variation among different groups was determined by One-Way ANOVA Analysis. And then, the difference between two groups was determined by Tukey-Kramer Multiple Comparison Test using Statcel Software. p value<0.05 was considered to be significantly different.

2. Results of Experiments

<Cell Sheet Creation Using mESC-Derived Cardiomyocytes and Fibroblast>

At first we evaluated the characterization of cells that we were going to use for the co-culture experiments. The phase contrast images revealed that cells isolated from neonatal hearts, adult hearts and adult dermal tissue showed the fibroblast-like morphology (See FIG. 1A). Since there are not specific antibodies for fibroblasts, we tried to examine the expression of the proteins that are known to be expressed in fibroblasts such as DDR2 (CD167b), vimentin and αSMA. As shown in FIGS. 1B to 1E, almost all of each type of cells expressed DDR2, vimentin and αSMA, but not Calponin (smooth muscle cell marker), Cytokeratin (epithelial cell marker) and NG2 (pericyte marker). On the basis of these findings, we used these cells as fibroblasts following experiments.

Figure 2:
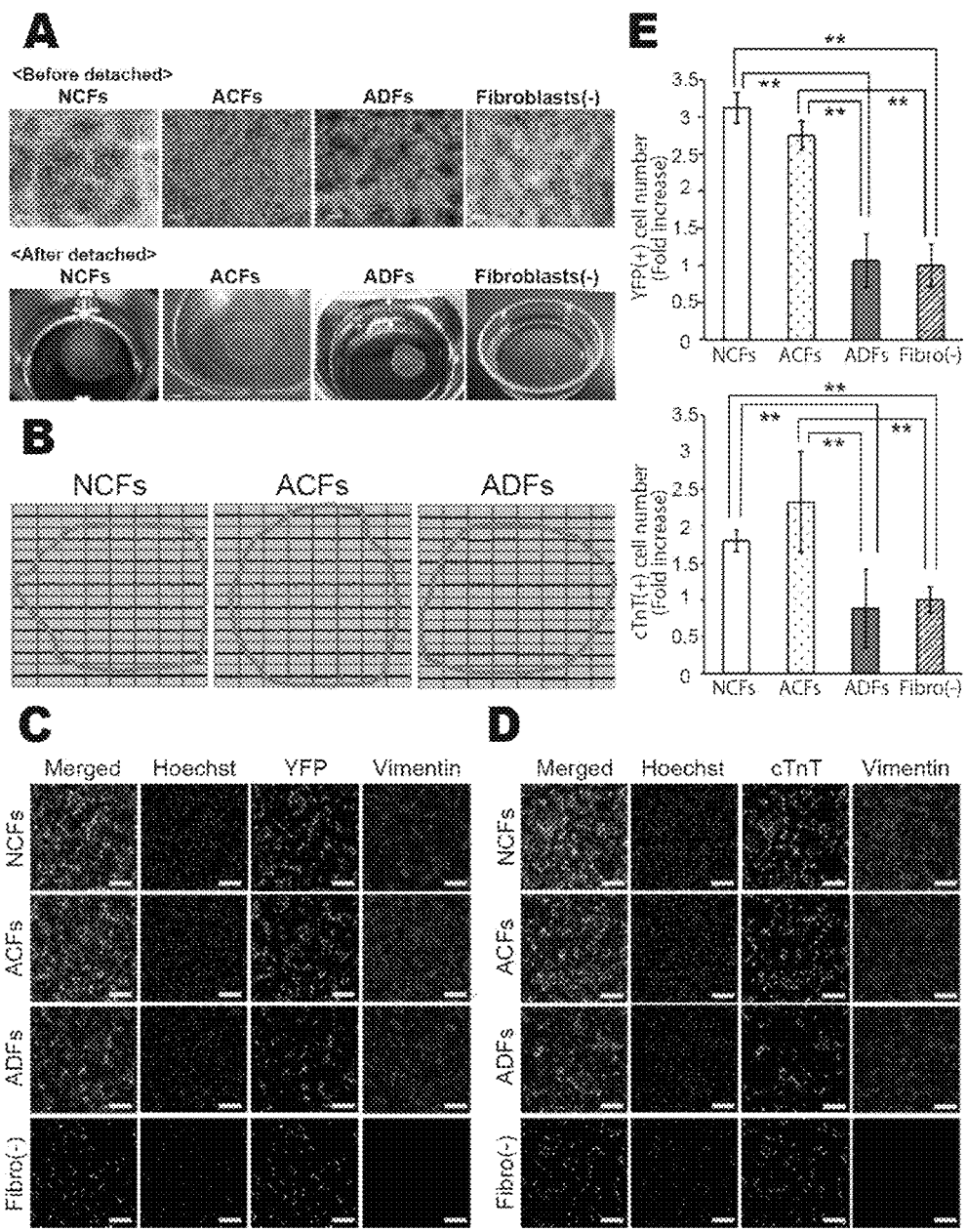
[FIG. 2] Differences in characteristics of mESC derived cardiac cell sheets that were co-cultured with fibroblasts (photographs). (A) Before separated, many cell masses that were autonomously beating were observed on NCF and ACF co-culture sheet. After decrease in temperature, cell sheet formation was not observed in mESC derived cardiomyocytes and fibroblasts (−). (B) Extracellular action potentials on each of the cell sheets. Action potentials in ACF or NCF co-culture sheet were observed in each channel. However, the action potentials occurred on a one-off basis on the ADF co-culture sheet (encircling lines indicate the shapes of the cell sheets). (C) Immunofluorescent stain in each of the cell culture dishes which were observed by a confocal microscope. YFP emitted green (yellow) fluorescence (YFP: excitation wavelength 514 nm, fluorescence wavelength 527 nm), and vimentin emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). The confocal microscopy observation suggested that, the cells co-cultured with NCF or ACF have a large number of YFP (+) cells, compared with the cells co-cultured with fibroblasts (−) or ADF. (D) Immunofluorescent stain in each of the cell culture dishes observed by a confocal microscopy. cTnT was stained by Cy5 (Cy5: excitation wavelength 650 nm, fluorescence wavelength 530 nm), vimentin emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). The confocal microscopy observation suggested that, the cells co-cultured with NCF or ACF have a large number of cTnT (+) cells, compared with the cells co-cultured with fibroblasts (−) or ADF. (E) The bar graphs show increase in the numbers of YFP (+) cells or of cTnT (+) cells in each of the cell culture dishes. The numbers of YFP (+) cells or of cTnT (+) cells in fibroblasts (−) were set to 1. More numbers of YFP (+) cells and cTnT (+) cells were observed in NCF or ACF culture dish compared with those in the culture dish of ADF co-culture or fibroblasts (−). In addition, there is no significant relationship in the number of cardiomyocytes between NCF and ACF. (N=3, ** P<0.01)

According to our previous findings that certain extent amounts of fibroblasts were necessary for fabricating cell sheet using mESC-derived cardiomyocytes and the optimal ratio of cardiomyocytes/fibroblasts was 8:2 (Biomaterials. 2011:32:7355-7362), we tried to create cardiac cell sheets using mESC-derived cardiomyocytes and 3 types of fibroblasts (ACFs, ADFs and NCFs) on UpCell temperature-responsive culture dishes. When cardiomyocytes were co-cultured with ACFs or NCFs, beating cardiomyocytes were equally distributed all over the area. Conversely, when cardiomyocytes were co-cultured with ADFs, nearby beating cells were aggregated. After 5 days cultivation, when the cultivation condition were changed from 37° C. to 20° C., monolayered cell sheets were created in every condition with fibroblasts, but not in the condition without fibroblasts (FIG. 2A).

Next we examined the electrophysiological evaluation of the cell sheets using a MED system (Biomaterials. 2011; 32:7355-7362, Biomaterials. 2006; 27:4765-4774). Consistent with the microscopical observation (FIG. 2A), the extracellular action potential was observed at each channel in cell sheets with ACFs and NCFs (FIG. 2B). Since it was recognized that, in these cell sheets, the entire sheets were uniformly beating, it was suggested that an electronic network was fabricated in the sheets and these cell sheets can carry out electric propagation. Meanwhile, in the cell sheets co-cultured with ADFs, the extracellular action potential was only observed in limited areas.

To confirm the difference of cardiomyocytes distribution among cell sheets, cofocal microscopic analysis was performed. As shown in FIGS. 2C to 2E, the number of YFP(+) cells and cardiac troponin T (cTnT) (+) cells, indicatives of mESC-derived cells, in cell sheets with ACFs and NCFs were more than those in cell sheets with ADFs. The number of cardiomyocytes in cell sheets with ADFs was comparable to that in condition without fibroblasts. In addition, there is no significant correlation on the number of cardiomyocytes between cell sheets co-cultured with ACFs and NCFs. These findings suggest that every kind of fibroblasts was useful for fabricating cell sheet, but fibroblasts derived from hearts might be better for fabricating more functional cardiac cell sheets.

<Cardiomyocyte Proliferation in Cellsheets>

Figure 3:
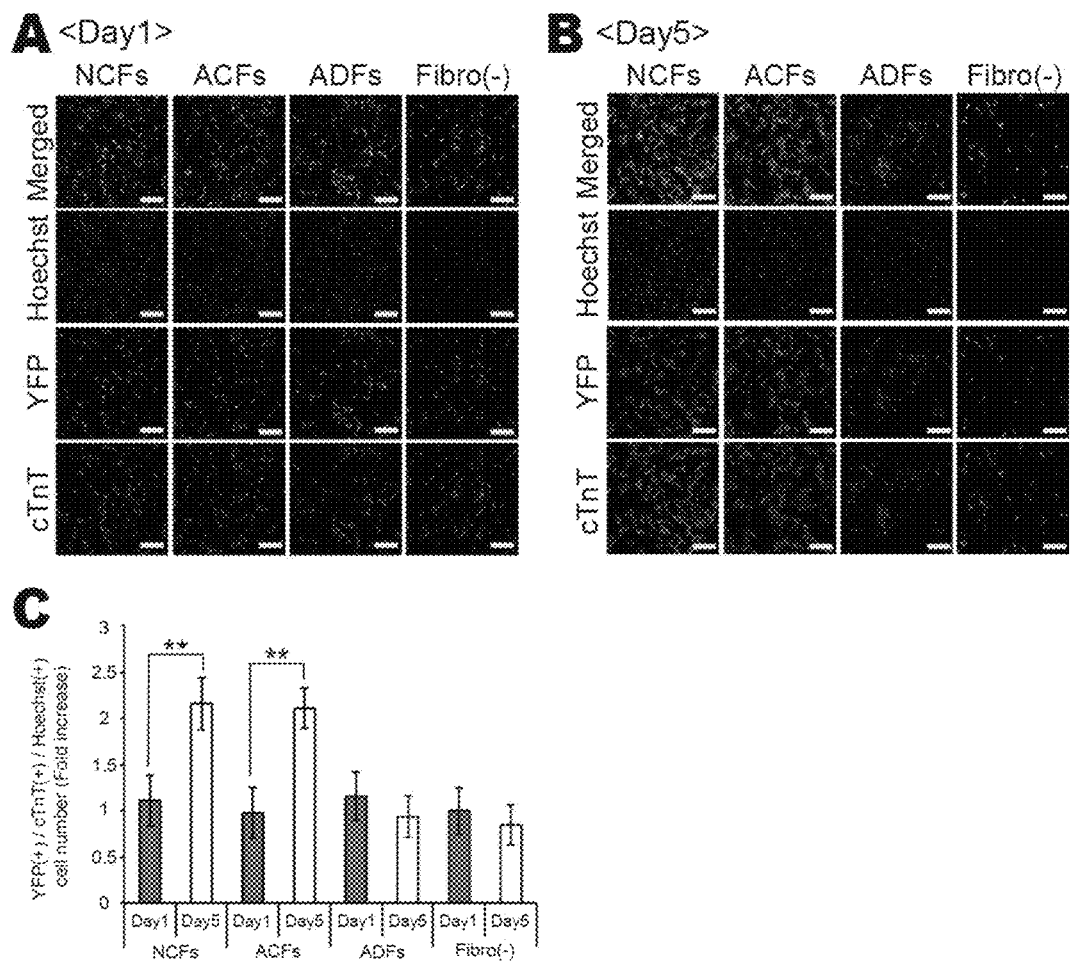
[FIG. 3] The number of cardiomyocytes at day 1 and day 5 from the cell culture start in each of the cell culture dishes (Photographs). (A) Immunofluorescent stain at day 1 from culture start in each of the cell culture dishes which were used in a confocal microscope. YFP emitted green (yellow) fluorescence (YFP: excitation wavelength 514 nm, fluorescence wavelength 527 nm), and cTnT emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). (B) Immunofluorescent stain at day 5 from culture start in each of the cell culture dishes which were observed by a confocal microscope. YFP emitted green (yellow) fluorescence (YFP: excitation wavelength 514 nm, fluorescence wavelength 527 nm), and cTnT emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). (c) The number of cardiomyocytes in each of the cell culture dishes. The bar graphs show increase in the numbers of YFP (+) cells and of cTnT (+) cells (The values at day 1 in fibroblasts (−) were set to 1). In the ACF and NCF culture dishes, more numbers of cardiomyocytes were observed at day 5 from culture start compared with those at day 1. However, in the other culture dishes, there was no difference in the number of cardiomyocytes between day 1 and day 5. No significant difference was observed between ACF and NCF. (N=3, ** P<0.01)

To investigate the cause of the different number of cardiomyocytes between cell sheets co-cultured with heart-derived fibroblasts and dermal tissue-derived fibroblasts, the number of cardiomyocytes was examined at day 1 and day 5 in co-culture (FIGS. 3A to C). At day 1, the number of cardiomyocytes was identical among conditions, suggesting that each type of fibroblasts did not affect the initial adherence of cardiomyocytes after seeding. In co-culture with ACFs and NCFs, the number of YFP (+) and cTnT (+) cardiomyocytes at day 5 was significantly higher than that at day 1. On the other hand, in co-culture with ADFs or in cardiomyocytes monoculture condition, the number of cardiomyocytes at day 5 was similar to that at day 1. The time-lapse image analysis using YFP(+) cardiomyocytes and fibroblasts isolated from DsRed mice showed that cardiomyocytes migrated and proliferated and constructed the mutual network formation in co-culture with NCFs. Conversely in co-culture with ADFs, cardiomyocytes showed less proliferation and did not construct the network formation. These findings suggest that fibroblasts from hearts, but not fibroblasts from dermal tissue might induce proliferation of mESC-derived cardiomyocytes in co-culture condition.

Figure 4:
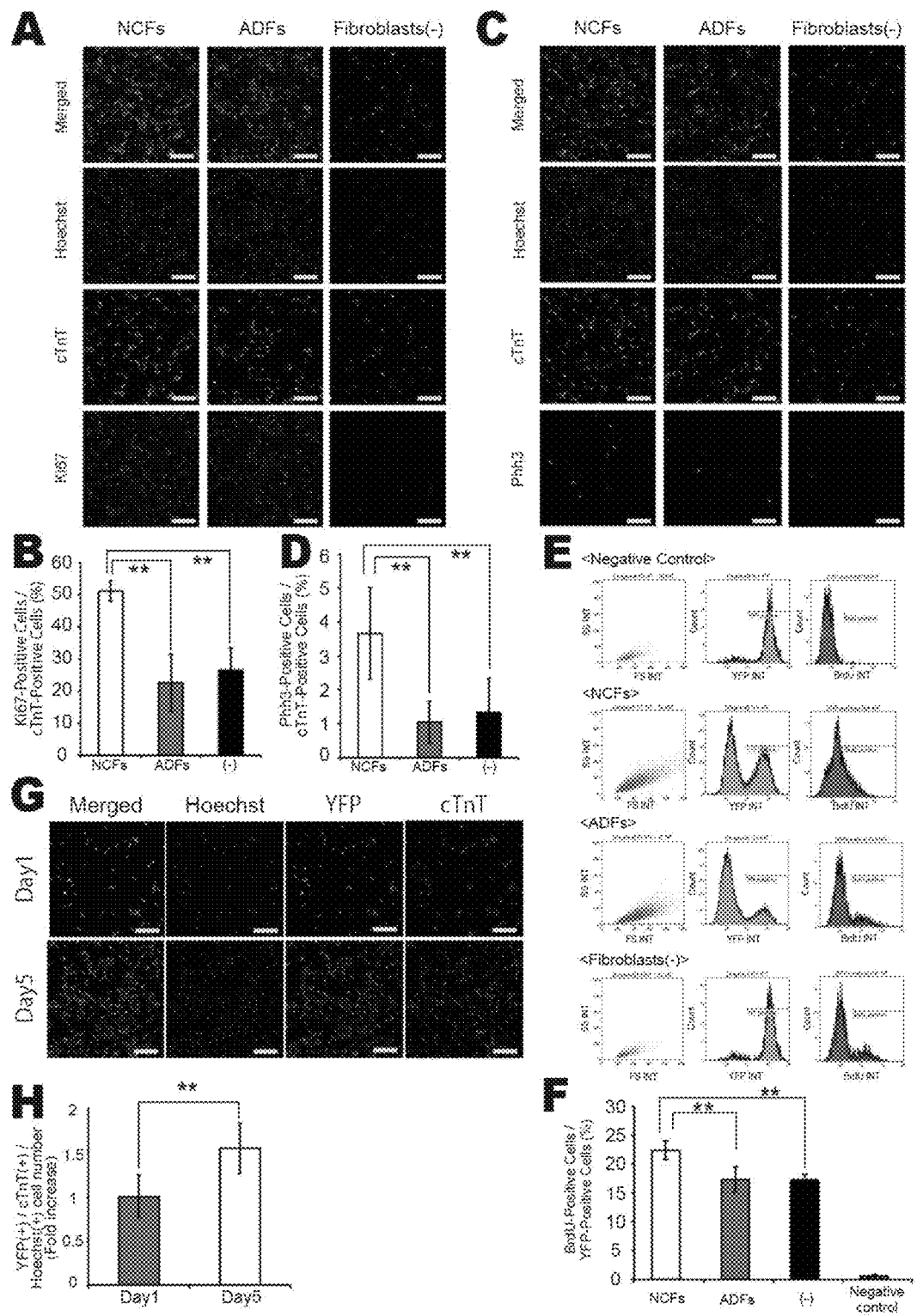
[FIG. 4] Evaluation of proliferation in cardiomyocytes by immunofluorescent stain (photographs). (A) Immunofluorescent stain observation of Ki67 positive cardiomyocytes in each of co-culture dishes by using the confocal microscope. cTnT was stained by Cy5 (Cy5:excitation wavelength 650 nm, fluorescence wavelength 530 nm), and Ki67 emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). (B) Percentage of Ki67 (+) or phosphorylated histone 3 (phosphor S10; Phh3) (+) cardiomyocytes in each of the culture dishes (N=4,  P<0.01). (C) Immunofluorescence stain observation of phosphorylated histone 3 (phosphor S10; Phh3) positive cardiomyocytes in each of the culture dishes by using the confocal microscope. cTnT was stained by Cy5 (Cy5:excitation wavelength 650 nm, fluorescence wavelength 530 nm), and phosphorylated histone 3 (phosphor S10; Phh3) emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). (D) Percentage of phosphorylated histone 3 (phosphor S10; Phh3) (+) cardiomyocytes in each of the culture dishes (N=4,  P<0.01). (E) (F) BrdU FACS assay of cardiomyocytes in each of the culture dishes (N=3,  P<0.01). (G) Immunofluorescence stain observation of YFP (+) and of cTnT (+) at day 1 and day 5 from culture start in the insert culture dishes by using the confocal microscope. YFP emitted green (yellow) fluorescence (YFP: excitation wavelength 514 nm, fluorescence wavelength 527 nm), and cTnT emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). (H) The bar graphs show increase in the numbers of YFP (+) cells and of cTnT (+) cells at day 1 and at day 5. The numbers of YFP (+) cells and of cTnT (+) cells at day 1 were set to 1. The proliferation of cardiomyocytes was observed at day 5 (N=4,  P<0.01).

The proliferation of cardiomyocytes among conditions was confirmed by the immune cytochemical analysis. As shown in FIG. 4A to D, the percentage of Ki67(+) cells and phospho histone H3 (PHH3) (+) cardiomyocytes in co-culture with NCFs were significant higher than those in co-culture with ADFs and in cardiomyocytes monoculture condition. Furthermore BrdU incorporation assay also showed the significant increase of the percentage of proliferative cardiomyocytes in co-culture with NCFs compared with that in co-culture with ADFs and in cardiomyocytes monoculture condition (FIGS. 4E and F). These findings strongly suggest that heart-derived fibroblasts induce proliferation of cardiomyocytes.

To investigate the underlying mechanisms on the proliferation of cardiomyocytes in co-culture with NCFs, mESC-derived cardiomyocytes and NCFs were cultured using cell culture inserts. In this experiment, NCFs were cultured on the upper layer and cardiomyocytes were cultured on the lower layer. The number of cardiomyocytes at day 5 was remarkably higher than that at day 1 in the presence of NCFs (FIG. 4G). However, the degree of the increase on cardiomyocyte number in the cell culture insert experiments between day 1 and day 5 (~1.8 times) (FIG. 4H) was lower than that in co-culture condition (~2.5 times). These findings indicate it might promote the cardiomyocyte proliferation that the soluble factors secreted from NCFs and the cell-cell interaction between cardiomyocytes with cardiac fibroblasts.

<Comprehensive Genetic Analysis of NCFs and ADFs>

Figure 5:
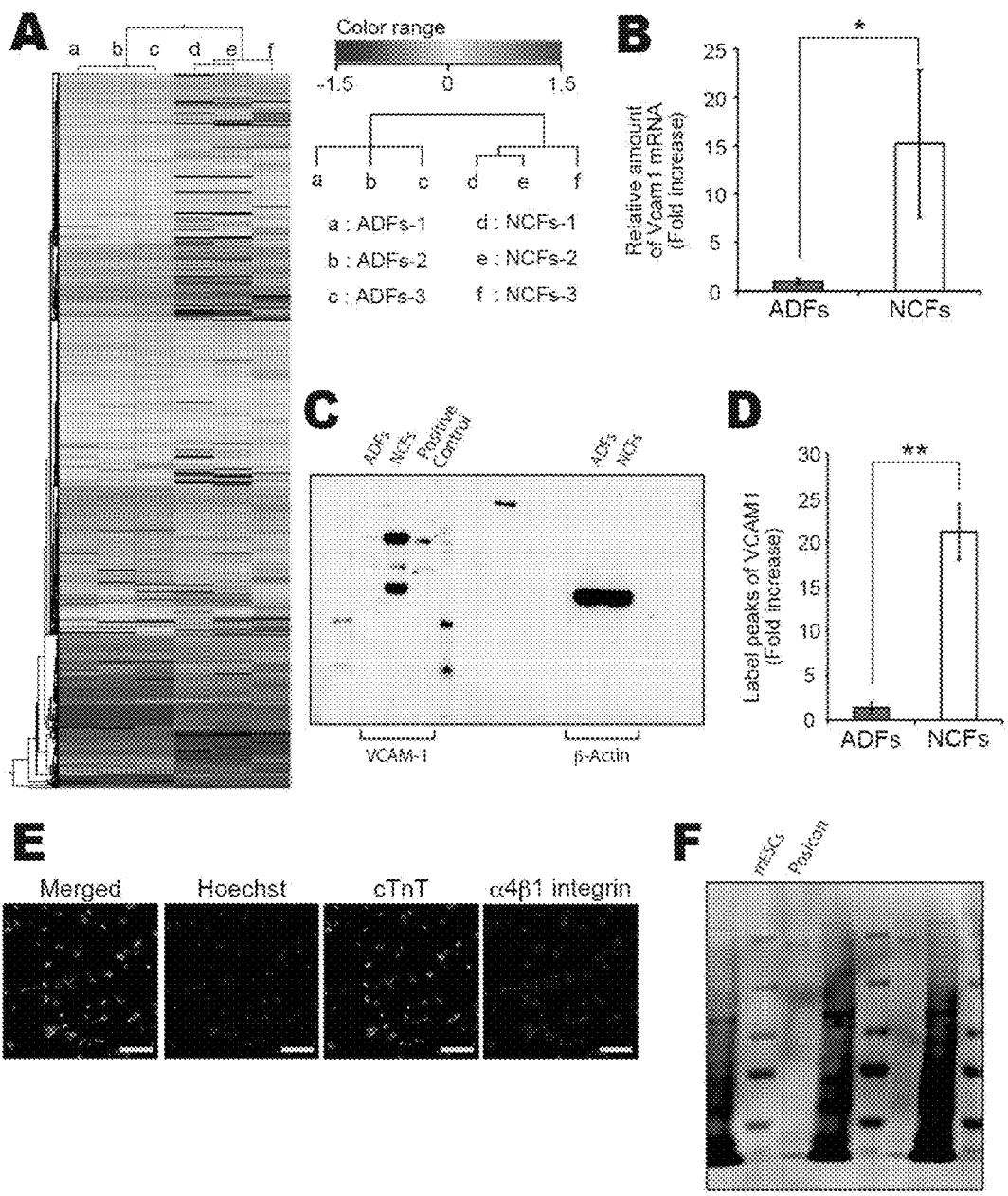
[FIG. 5] (A) Comprehensive gene cluster analysis of ADF and NCF (photograph). This gene heat map shows a remarkable difference between ADF and NCF. This map was divided into two groups. The first group consisted of only ADF, and the second group consisted of only NCF. (B) The VCAM-1 gene expression level was examined by real time PCR. The VCAM-1 expression level was significantly high in NCF. The number of VCAM-1 genes in NCF was 16 times higher than that in ADF (N=3,*P<0.05). (C-D) The expression level of VCAM-1 protein in NCF and ADF in western blot analysis. The following transient overexpression cell lysate was used as a positive control: Sol8 (SantaCruz, Calif., USA). The label peak of β-actin of each cell was set to 1 (N=3, ** P<0.01). (E) Immunofluorescence stain of the VCAM-1 receptor (α4β1) on mESC derived cardiomyocytes. (F) Western blot analysis of the VCAM-1 receptor on mESC derived cardiomyocytes. The following transient overexpression cell lysate was used as a positive control: Jurkat whole cell lysate.

To identify the factors that are responsible for involved in these effects, we performed comprehensive genetic analysis between NCFs and ADFs using a microarray analysis. As shown in FIG. 5A, many differences in gene expression were observed between NCFs and ADFs. Over 500 genes showed more than 10 times enhanced expression in NCFs compared with ADFs. After choosing the cardiovascular-related genes from the lists, 20 genes were remained. Furthermore when we selected genes that were reported the embryonic lethal phenotype causing a disorder to generate heart in knock out mouse model and also act as a soluble factor and an sdhesive factor, Vcam-1 was remained. The enhanced expression of Vcam-1 in NCFs compared with ADFs was confirmed by quantitative RT-PCR and western blot analysis (FIGS. 5B to D).

<VCAM-1-Dependent Cardiomyocyte Proliferation in Co-Culture with Cardiac Fibroblasts>

Since integrin α4β1 is known to be the principal co-receptor of VCAM-1, we examined the integrin α4β1 expression in mESC-derived cardiomyocytes. As shown in FIGS. 5E and F, almost all of mESC-derived cardiomyocytes showed generation of integrin α4β1.

Figure 6:
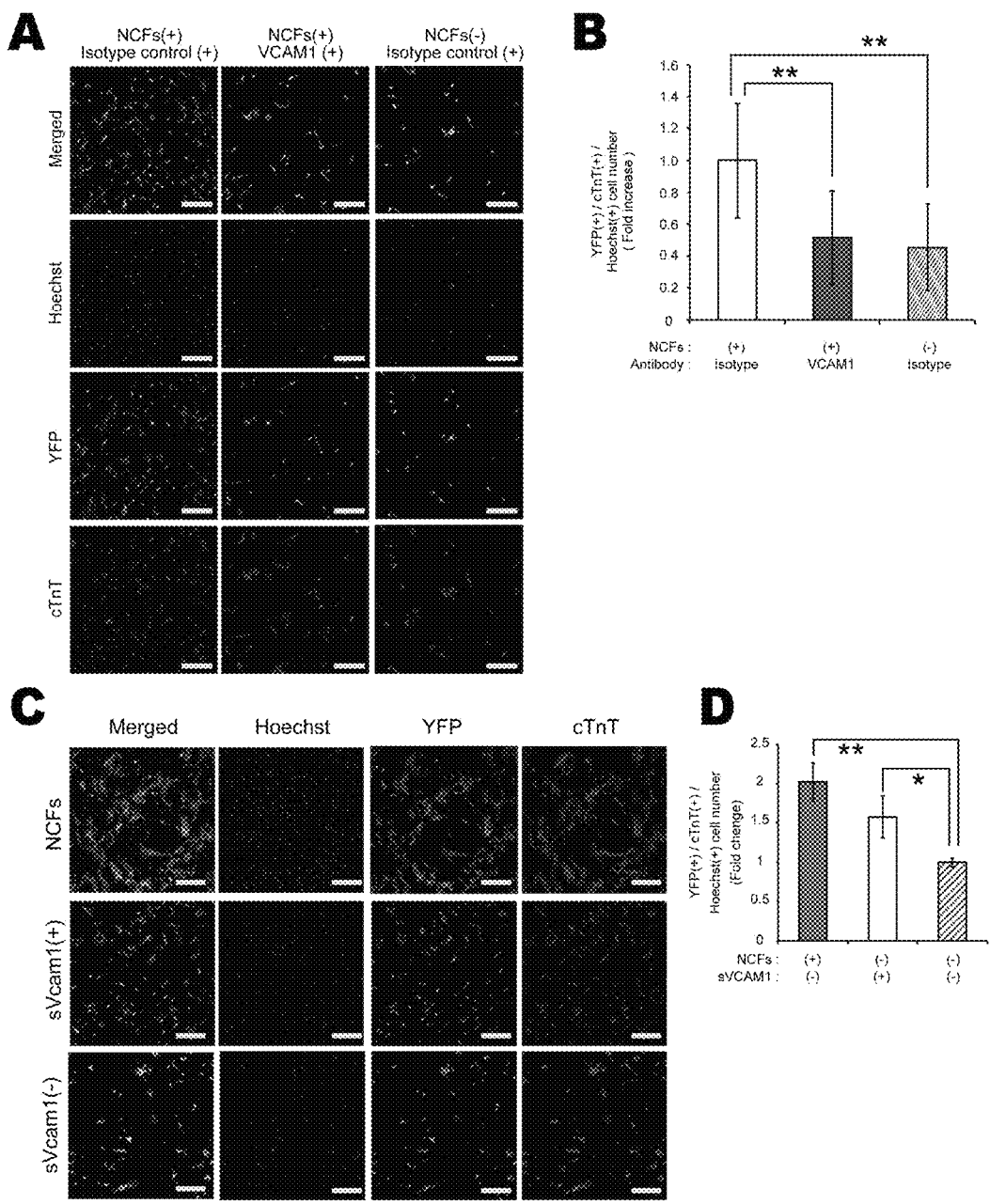
[FIG. 6] Identification of cardiac growth factor by immunofluorescence stain analysis (photographs). (A-B) Immunofluorescence stain observation of the effect of neutralizing antibodies on cardiomyocytes at day 5. YFP emitted green (yellow) fluorescence (YFP: excitation wavelength 514 nm, fluorescence wavelength 527 nm), and cTnT emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). When NCF and cardiomyocytes were co-cultured by using a VCAM-1 neutralizing antibody, the number of cardiomyocytes was decreased at day 5. Meanwhile, when an isotype control was used, there was no effect on the number of cardiomyocytes at day 5. (N=3, ** P<0.01). (C-D) Immunofluorescence stain observation of the effect of VCAM-1 soluble protein on cardiomyocytes at day 5. YFP emitted green (yellow) fluorescence (YFP: excitation wavelength 514 nm, fluorescence wavelength 527 nm), and cTnT emitted red fluorescence (cy3: excitation wavelength 512 nm, fluorescence wavelength 552 nm), and the nucleus was stained in hoechst 33258 (blue) (hoechst 33258: excitation wavelength 352 nm, fluorescence wavelength 461 nm). Cardiomyocyte growth effect was obtained by culturing with VCAM-1 soluble protein (10 μg/mL). Moreover, the number of cardiomyocytes on Day 5 was comparable to that in co-culture with NCFs. (N=3,*P<0.05, ** P<0.01).

Next we elucidated whether VCAM-1 contributed to cardiac fibroblasts-mediated cardiomyocyte proliferation using neutralizing antibodies. After the pretreatment of NCFs with anti-VCAM-1 antibodies, NCFs and mESC-derived cardiomyocytes were cultured using cell culture inserts. Anti-VCAM-1 antibody treatment significantly inhibited cardiac fibroblast-mediated increase of cardiomyocyte number (FIGS. 6A and B).

Finally we evaluated the direct effects of VCAM-1 on the proliferation of cardiomyocytes. One day after starting culture, cardiomyocytes were treated with VCAM-1 recombinant protein until day 5. As shown in FIGS. 6C and D, VCAM-1 treatment increased the number of cardiomyocytes compared with control. These findings suggest heart-derived fibroblasts might induce cardiomyocyte proliferation through fibroblasts-mediated VCAM-1 and integrin α4β1 in cardiomyocytes.

To confirm importance of VCAM-1 positive cells in constructing functional cardiac cell sheets, we measured the percentage of VCAM-1 positive cells in organism-derived cardiac fibroblasts.

Cardiac fibroblasts were dissected and collected from neonatal mice (1 day) of C57/BL6 mice, and skin fibroblasts were dissected and collected from adult mice (10-12 weeks). Each of the fibroblasts were adhesion-cultured up to passage 3, and the cell volume of $1 \times 10^7$ cells per condition was obtained. Passage 3 is the same condition with the culture condition of the above-mentioned cardiomyocytes produced by cell sheets.

Both fibroblasts were subjected to primary immunofluorescent stain with Goat polyclonal anti-VCAM-1 antibodies (R&D systems, Minneapolis, Minn.), and were subjected to secondary immunofluorescent stain with Alexa Fluor 488 Donkey anti-goat IgG (Life Technologies, MD, United States). Subsequently, FACS analysis was conducted at Gallios (Beckman Coulter, Brea, Calif.), and VCAM-1 positive cell rate was measured (N=3). Calculation of significant difference was carried out by Student's t-test.

Figure 7:
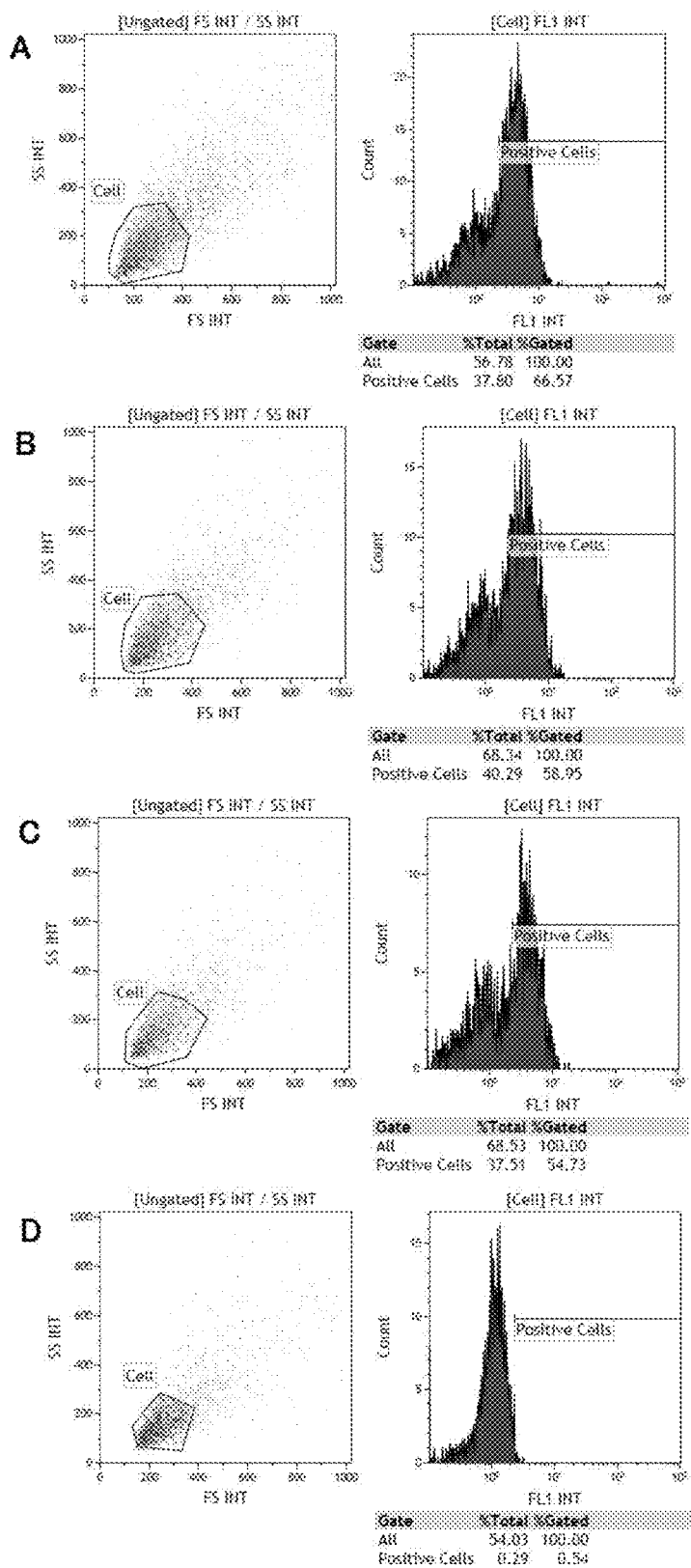
[FIG. 7] The results of FACS analysis of cardiac fibroblasts derived from neonatal mice. (A-C) The results of staining with an anti-VCAM-1 antibody are shown. (D) The result of a negative control by staining dermal fibroblasts only with a secondary antibody is shown.

The results of cardiac fibroblasts (NCFs) were shown in FIGS. 7A-C. It was found that the percentage of VCAM-1 positive cells in NCFs was approximately 60% (FIG. 7A: 66.57%, FIG. 7B: 58.95%, FIG. 7C: 54.73%). Conversely, the percentage of VCAM-1 positive cells in skin fibroblasts (ADFs) was approximately 5%, and it turned out that the percentage of VCAM-1 positive cells in NCFs is significantly more than that of ADFs ($P<0.001$).

It was suggested that cardiac fibroblasts containing many VCAM-1 positive cells contribute to construction of functional myocardial tissues by proliferating cardiomyocytes derived from mice ES through the expressing VCAM-1. Further, it was considered that VCAM-1 positive cardiac fibroblasts originate from an outer membrane-derived cell from the view point of embryology, and we obtained the suggestion that it is effective to classify fibroblasts from the view point of embryology, and not to conduct morphological classification but to conduct functional classification as a cell source for constructing a functional tissue.

It is considered that, in NCFs, the majority of the cells that are not expressing VCAM-1 express CD31 (vascular endothelial cell marker). The reason for this is as follows: it is known that tissue-resident cardiac fibroblasts are produced from epicardium-derived cells through epithelial mesenchymal transition (EMT), and also are differentiated from vascular endothelial cells through endothelial mesenchymal transition (EndMT). Furthermore, as is the case with cardiac fibroblasts, kidney fibroblasts that differentiate from vascular endothelial cells through EndMT are expressing CD31 (J Am Soc Nephrol 19:2282-2287, 2008). This may also become one of the bases for supporting that NCFs are expressing CD31.

From the above, it was clarified that, not skin fibroblasts but cardiac fibroblasts enhance proliferation of mouse embryonic stem cell (mESC) derived cardiomyocytes, and contribute to construction of more functional cardiac cell sheets. Moreover, it was indicated that cardiac fibroblasts are more abundantly expressing VCAM-1 compared with skin fibroblasts, and that the VCAM-1 of cardiac fibroblasts play an important role in proliferation of cardiac cells and construction of cardiac tissues that are functionally biologically-designed.

Example 2

Example 1 reveals that when a myocardial tissue derived from a pluripotent stem cell is constructed, cardiac fibroblasts cause cell proliferation of cardiomyocytes through VCAM-1 which is protein highly expressed by the cardiac fibroblasts, prompt beating in the created whole myocardial tissue, and significantly improve the functionality. However, it is also revealed that cardiac fibroblasts have a heterozygous character even in a local area named heart, and that all the cardiac fibroblasts do not necessarily express VCAM-1. Therefore, we carry out a study to elucidate that, when fibroblasts are not classified by the morphological features in a conventional manner but are classified by protein expressed with molecular biology, to what extent cardiac fibroblasts expressing VCAM-1 (VCFs) should be compounded so as to create a highly functional myocardial tissue.

1. Experimental Method
(1) Animals and Reagents

Wild-type C57BL/6 mice were purchased from Japan SLC (Shizuoka, Japan). B6 Cg-Tg (CAG-DsRed*MST) 1Nagy/J mice were purchased from The Jackson Laboratory (Bar Harbor, Me.). All the experimental protocols were approved by The Keio University Institutional Animal Care and Use Committee. The following antibodies were used for immunofluorescent staining and flow cytometry.

guinea pig monoclonal anti-vimentin (Progen, Heidelberg, Germany), mouse monoclonal anti-cardiac troponin T (cTnT) (Thermo Scientific, Rockford, Ill.), rabbit polyclonal anti-Ki67 (Abcam), Rat monoclonal anti-VCAM-1 (Biotin) (Abcam), Rat monoclonal anti-CD31 (Abcam), Rabbit monoclonal anti-VCAM-1 (Abcam).

Secondary antibodies were purchased from ImmunoResearch Laboratories (West Grove, Pa.).

(2) Culture of Mouse ES-Derived Cardiomyocytes

Maintenance, cardiomyocyte differentiation, and purification of mouse ES cells (mESC) that express neomycin phosphotransferase genes under the control of α-myosin heavy chain promoter, and that express yellow fluorescent protein (YFP) are conducted in accordance with the method as described previous report (Matsuura K, et al., Biomaterials. 2011; 32:7355-7362).

Briefly described, for the purposes of induction to cardiomyocytes and cardiomyocyte purification, $5 \times 10^4$ cells/mL of trypsin-treated ES cells (total 125 mL/flask) were seeded to a spinner flask (Integra Biosciences, Zizers, Switzerland), and cultured with DMEM supplemented with 10% FBS for 10 days, and subsequently the differentiated cells were treated with neomycin for 8 days.

Mouse ES-derived cardiomyocytes (Cor.At) to which puromycin resistance gene and green fluorescent protein (GFP) were introduced under α-myosin heavy chain promoter were purchased from Axiogenesis AG (Cologne, Germany). Mouse ES-derived cardiomyocytes were treated with puromycin for 2 days, and were cultured in a medium not containing puromycin for 2 weeks.

(3) Isolation of VCAM-1 Positive Cardiac Fibroblasts

Cardiac fibroblasts isolated from a one day old wild-type C57BL/6 neonatal mouse were cultured, and VCFs were isolated with a magnetic cell sorter (Magnetic-activated cell sorting, MACS). The isolated VCFs were re-cultured, and an experiment was carried out after removing dead cells.

(4) Immunofluorescent Staining

Cells were fixed with 4% paraformaldehyde, and immunofluorescent staining was carried out. The immunofluorescent-stained cells were analyzed with a confocal quantification image cytometer CQ1 (Yokogawa Electric Corporation, Tokyo, Japan).

(5) Flow Cytometry

Tissues of the heart collected from a wild-type C57BL/6 mouse were dissociated with gentleMACS Octo Dissociator (Miltenyi Biotec, Gladbach, Germany), and homogenized to the cellular level. The obtained cells were immunofluorescent-stained, and subsequently analyzed with an S3 cell sorter (BIO-RAD, CA).

(6) Time-Lapse Photography and Analysis

As evaluation of the ability of forming a network, YFP positive ES cell-derived cardiomyocytes and cardiac fibroblasts isolated from a DsRed mouse were co-cultured, and the inside of a BZ-9000 fluorescent microscope was kept at the concentration of 5% CO2 at 37° C., and time-lapse observation was carried out for 5 days (Keyence, Osaka, Japan). With respect of the evaluation of the migratory ability of a single cardiomyocyte, GFP expressing type cardiomyocytes were seeded at the concentration of $5.45 \times 10^4$ cells/cm$^2$, and fibroblasts isolated with MACS were seeded at the concentration of $1.36 \times 10^4$ cells/cm$^2$, which were weaker than the concentration at the time when a myocardial tissue was constructed, and time-lapse photography was carried out with a BZ-X700 fluorescent microscope for 3 days. The photographed time-lapse images were analyzed with a Motion Analyzer so as to calculate the total migratory distance (mm) of cardiomyocytes for three days of culturing, and the evaluation of the migratory ability was carried out (Keyence).

2. Results

Optimum Compounding Concentration Rates of VFCs and Cardiomyocytes

Figure 8:
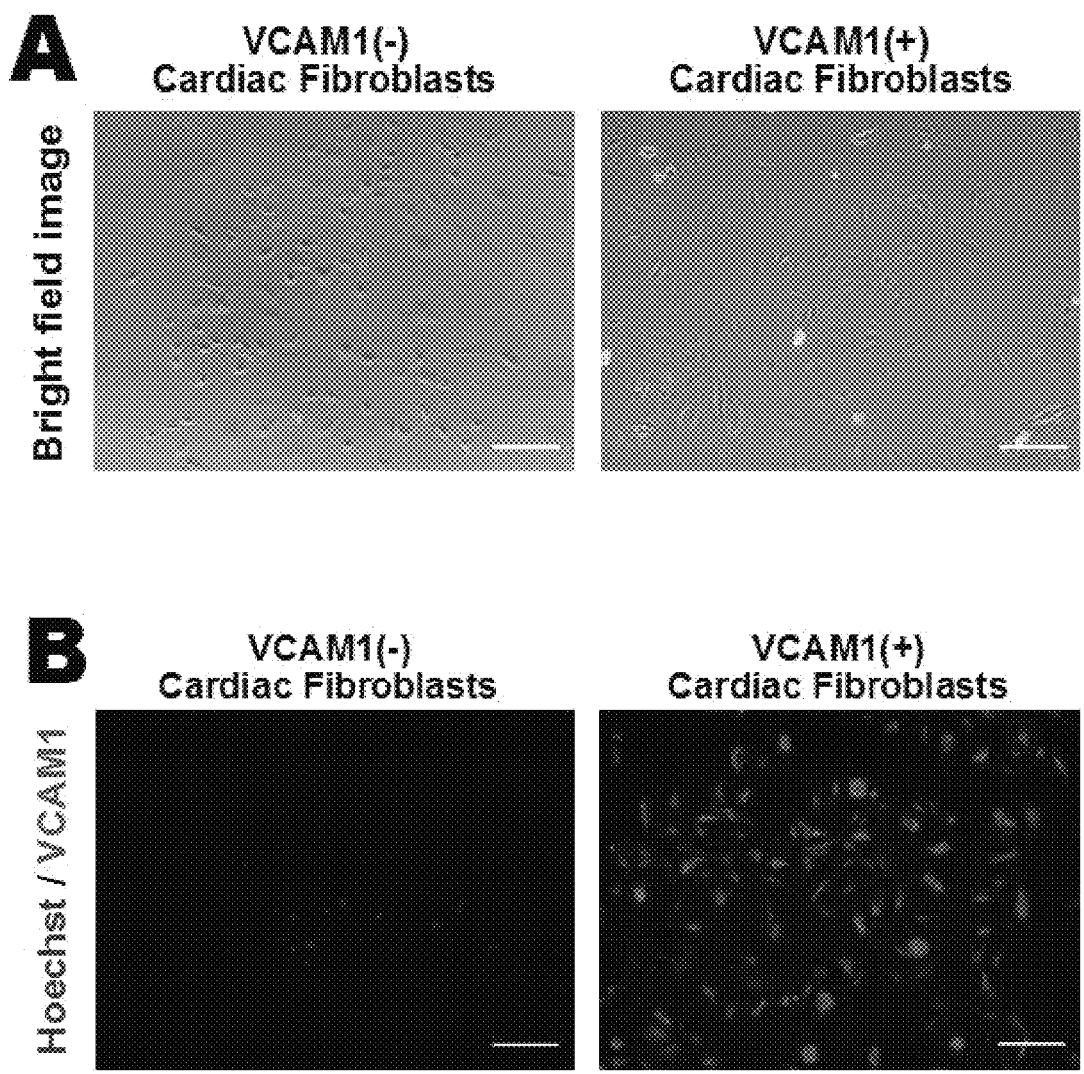
[FIG. 8] The optimum compounding concentration of VCAM-1(+) cardiac fibroblasts. (A) Phase difference images of VCFs (VCAM-1(+)) and VNCFs (VCAM-1(−)) isolated by a magnetic cell separator (MACS). (B) Fluorescence images (photographs) of VCFs (VCAM-1(+)) and VNCFs (VCAM-1(−)) isolated by a magnetic cell separator (MACS). VCAM-1 emits red fluorescence, and Hoechst 33258 emits blue fluorescence. Scale bar=200 µm.

It was found out that both of VCFs and VACM-1 negative cardiac fibroblasts (VNCFs) that were isolated and cultured with MACS show a fusiform fibroblast-like morphology in phase difference images (FIG. 8A). However, by using immunofluorescent staining, while expression of VCAM-1 protein emitting red fluorescence was observed in almost all the cells in VCFs, expression of VCAM-1 protein was not observed in VNCFs (FIG. 8B).

Subsequently, VCFs and VNCFs collected from cardiac fibroblasts and dermal fibroblasts were co-cultured with cardiomyocytes at each compounding ratio (Table 1), the highest mitogenic effect of cardiomyocytes was observed at Day 5 under the condition where 20% of VCFs and 80% of cardiomyocytes were seeded (FIGS. 9A and 9B). In addition, when the number of fibroblast were calculated by deducting the number of triple-positive cells of cTnT/GFP/Hoechst from the total number of Hoechst 33258 positive nuclei in a myocardial tissue at day 5 to which VCFs was compounded at 20%, it was revealed that cardiomyocytes existed at 9.5%, and fibroblasts existed at 90.5% (FIG. 10).

TABLE 1

| | Compounding ratio of each type of cell | | | | |
|---|---|---|---|---|---|
| Sample | Cardio-myocytes | VCAM1(+)NCFs | VCAM1(−)NCFs | NCFs | ADFs |
| A | 80% | — | — | — | 20% |
| B | 80% | 0% | 20% | — | — |
| C | 80% | 4% | 16% | — | — |
| D | 80% | 8% | 12% | — | — |
| E | 80% | 12% | 8% | — | — |
| F | 80% | 16% | 4% | — | — |
| G | 80% | 20% | 0% | — | — |
| H | 80% | — | — | 20% | — |

Evaluation of Migratory Ability of Cardiomyocytes

Figure 11:
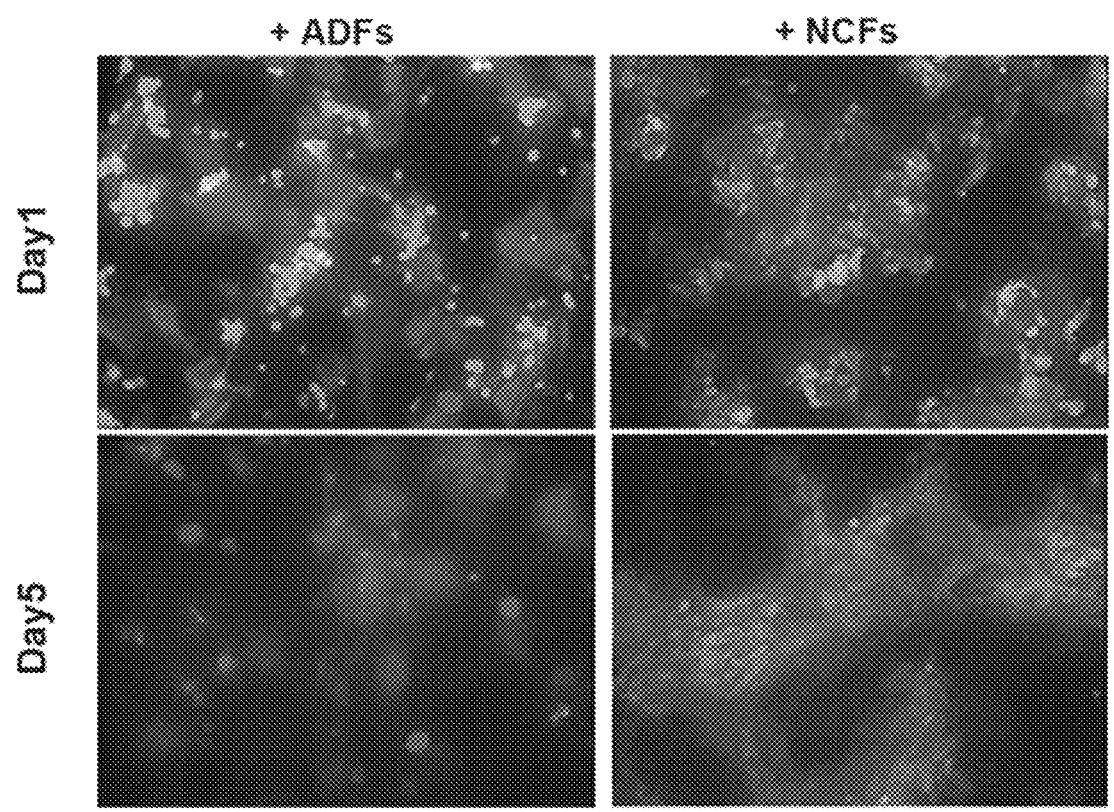
[FIG. 11] Evaluation of division (proliferation) effect, migration effect and ability of constructing a network of cardiomyocytes for 5 days of culturing under the condition of co-culturing with NCFs and ADFs (photographs). YFP expressing cardiomyocytes emit green fluorescence, and DsRed fibroblasts emit red fluorescence. Magnification is ×200.

It was revealed by time-lapse photographing that, when YFP positive ES cell-derived cardiomyocytes and cardiac fibroblasts isolated from a DsRed mouse were co-cultured, cardiomyocytes were divided at day 5, and a strong network was constructed (FIG. 11). As mentioned before, cardiac fibroblasts prompt cell division of cardiomyocytes through the expressing VCAM-1 protein. VCFs and VNCFs isolated with MACS were co-cultured with GFP expressing type cardiomyocytes, and the total migratory distance (mm) of the cardiomyocytes for 3 days of culturing was calculated by time-lapse photographing, and the evaluation of migratory ability was carried out. It was revealed that, when VCFs were compounded, the number of GFP positive cardiomyocytes grows, and it was suggested by video analysis that the migratory ability of cardiomyocytes was significantly high, and took part in forming of a high level network (FIG. 12).

Evaluation of Localization of VCFs in a Biological Heart

Figure 9:
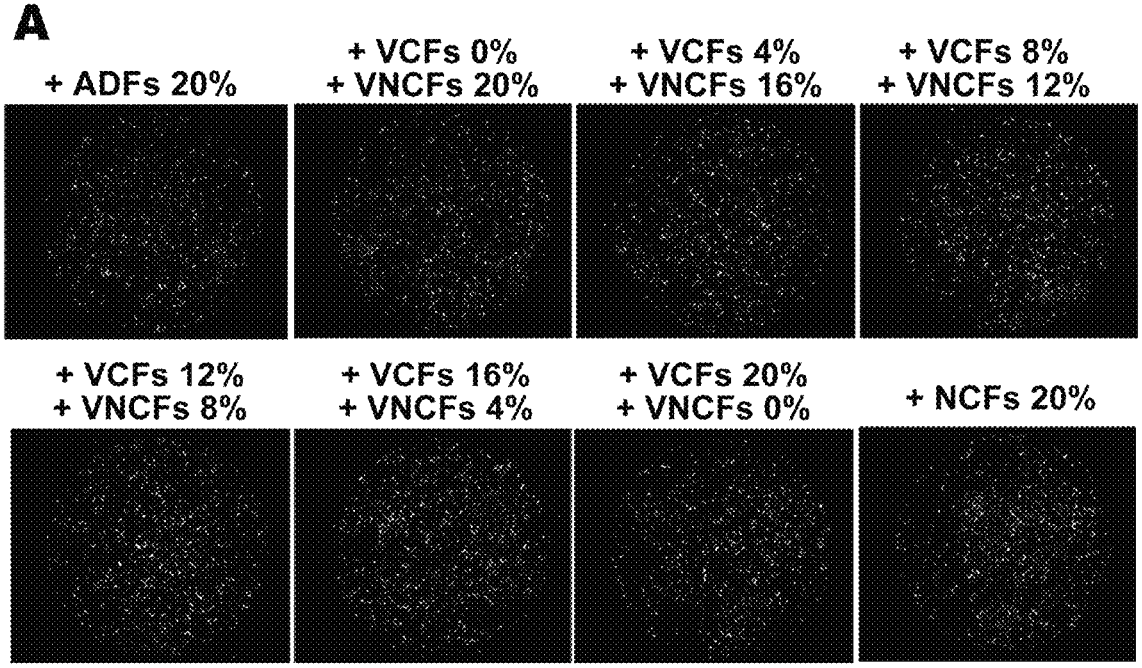
[FIG. 9] Evaluation of optimum compounding ratio of VCFs. (A) Fluorescence images (photographs) showing the results of co-culturing cardiomyocytes expressing GFP with ADFs, NCFs, or VCFs and/or VNCFs. ADFs=mouse adult-derived dermal fibroblasts, VCFs=VCAM-1 positive mouse neonatal cardiac fibroblasts, VNCFs=VCAM-1 negative mouse neonatal cardiac fibroblasts, and NCFs=neonatal mouse cardiac fibroblasts. GFP cardiomyocytes emit green fluorescence, and Ki 67 emits red fluorescence, and cTnT was stained by Cy5 (Cy5:excitation wavelength 650 nm, fluorescence wavelength 530 nm). Magnification is ×20. (B) A bar graph showing the results of co-culturing cardiomyocytes expressing GFP with ADFs, NCFs, or VCFs and/or VNCFs. The numbers of GFP (+) cells and cTnT (+) cells were set to 1 when cardiomyocytes and ADFs were co-cultured at the concentrations of 80% and 20%, respectively. N=4, **P<0.01.
Figure 9:
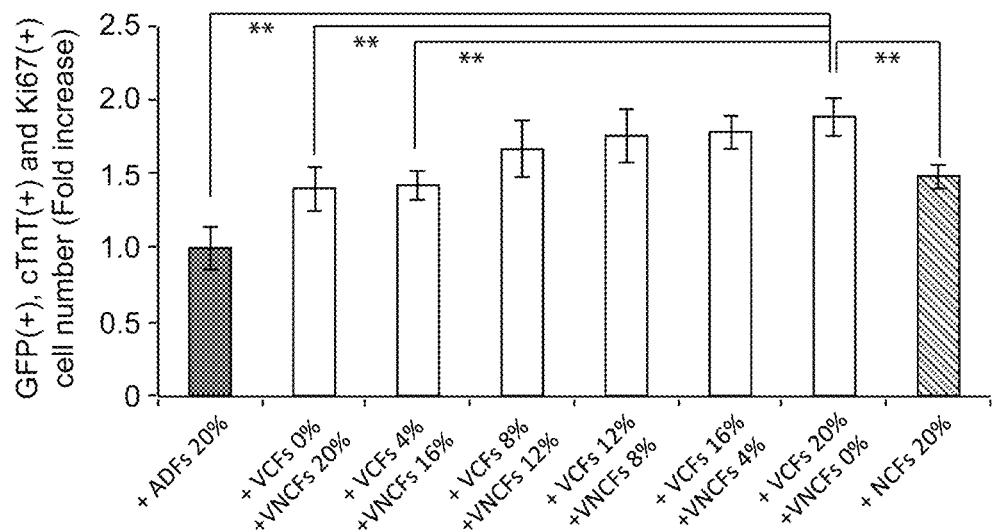
Figure 10:
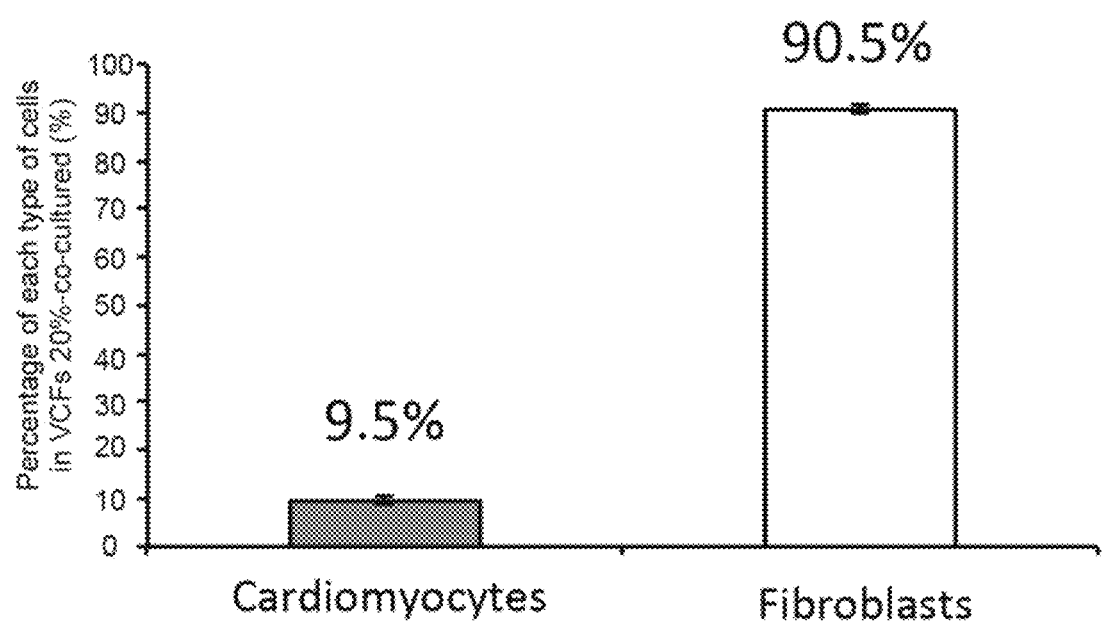
[FIG. 10] Evaluation of localization (N=4) of cardiomyocytes and fibroblasts at day 5 in a tissue created at the concentration of 80% cardiomyocytes and 20% VCFs.
Figure 12:
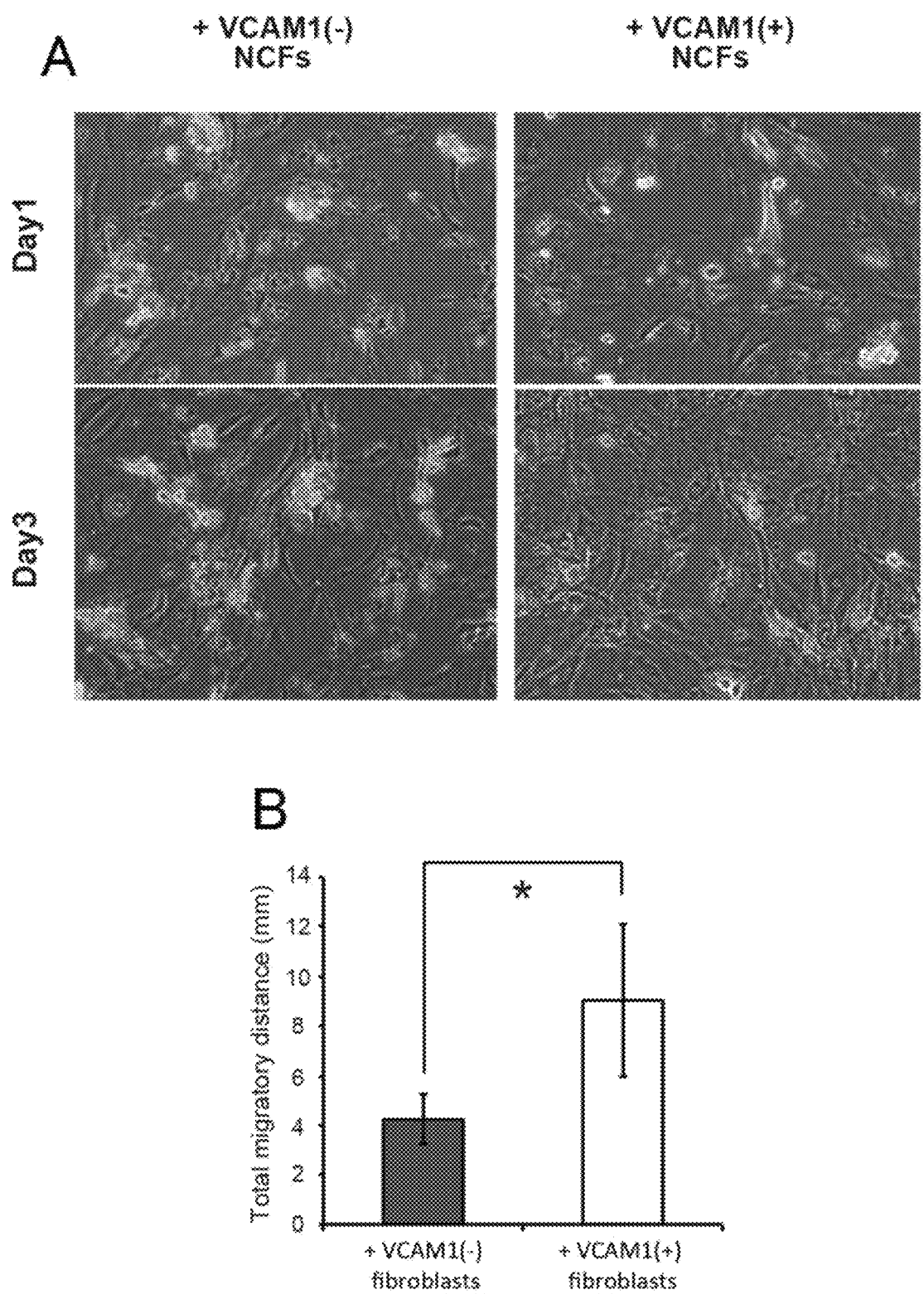
[FIG. 12] A shows fluorescence images indicating division (proliferation) of cardiomyocytes for three days of culturing at the time when co-culturing ES-derived cardiomyocytes with VCFs (VCAM-1 (+)) or VNCFs (VCAM-1 (−)) (photographs). GFP expressing cardiomyocytes emit green fluorescence. Magnification is ×100. B shows the results evaluating the migratory ability by calculating the total migratory distance for 3 days of culturing at the time when co-culturing ES-derived cardiomyocytes, and VCFs or VNCFs. N=5, *P<0.05.
Figure 13:
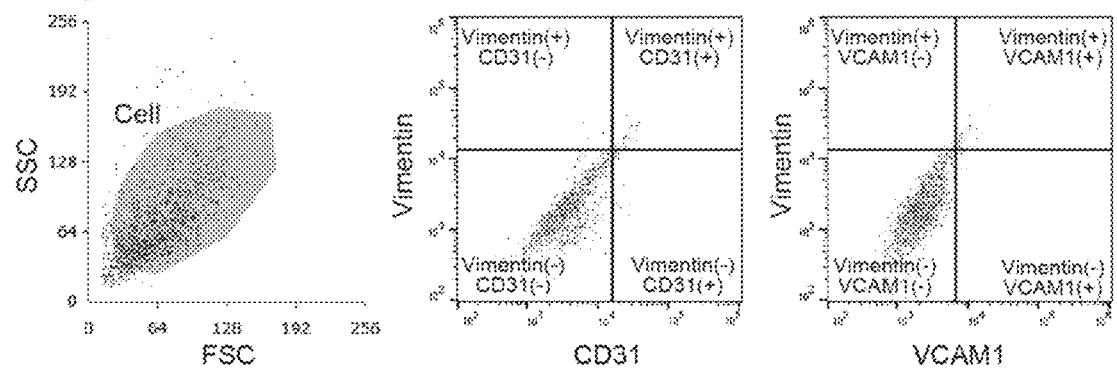
[FIG. 13] The results of analyzing the localization of Platelet Endothelial Cell Adhesion Molecule-1 (PECAM-1, CD31) and VCAM-1 positive cardiac fibroblasts with flow cytometry.
Figure 13:
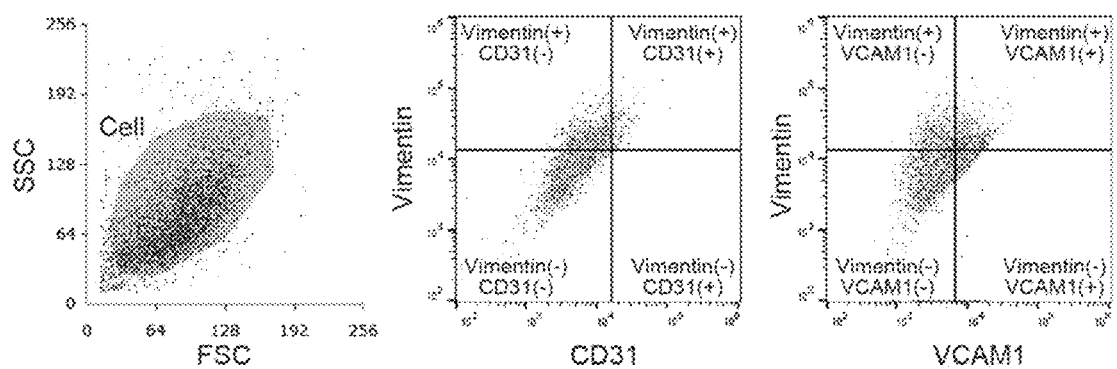
Figure 14:
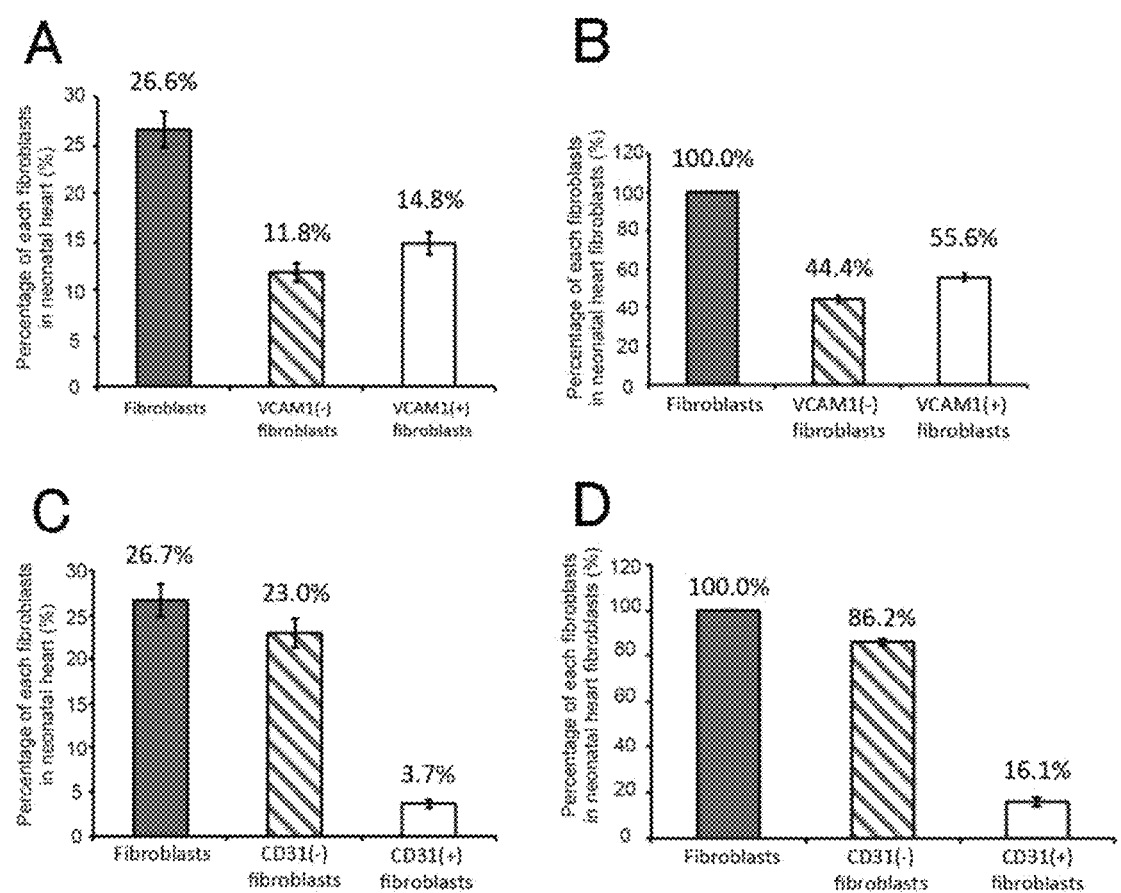
[FIG. 14] (A) Localization of VCFs in a biological heart (N=3). (B) Localization of VCFs in cardiac fibroblasts (N=3). (C) Localization of CD31-positive fibroblasts in a biological heart (N=3). (D) Localization of CD31 positive fibroblasts in cardiac fibroblasts (N=3).

It was revealed that, when a myocardial tissue was constructed by co-culturing at the concentration of 20% VCFs and 80% cardiomyocytes, cardiomyocytes grew at the highest level in the myocardial tissue, and obtained high migratory ability (FIGS. 9, 11 and 12). Further, it was revealed that 9.5% cardiomyocytes and 90.5% fibroblasts existed in a myocardial tissue created under the above-mentioned condition (FIG. 10). In order to evaluate whether the localization of cardiomyocytes and fibroblasts was different from a biological heart, a heart of a one day old mouse was collected, and crushed into the cellular level by enzyme treatment, and the evaluation of localization of cardiomyocytes and VCFs were carried out with flow cytometry. It was revealed that VCFs existed at 14.8% in the heart, and that 55.6% of fibroblasts expressed VCAM-1 protein (FIGS. 13, 14A and 14B). Moreover, it was revealed that fibroblasts that express CD31 existed at 3.7% in the heart, and that 16.1% of cardiac fibroblasts expressed CD31 protein (FIGS. 13, 14C and 14D).

3. Conclusion

The present study revealed that the optimum seeding concentration of VCFs required to create a high functional myocardial tissue was 20% by evaluating the proliferation level of cardiomyocytes by compounding VCFs sorted by a magnetic cell separator (Magnetic-activated cell sorting, MACS) and ES cell-derived cardiomyocytes at each concentration.

Furthermore, it was revealed that the localization of cardiomyocytes and fibroblasts in a myocardial tissue with 20% VCFs at day 5 after culturing was 9.5% and 90.5%, respectively. When VCFs were seeded at the concentration of 20% and cardiomyocytes were seeded at the concentration of 80%, and the evaluation of the migratory ability of cardiomyocytes was carried out for 3 days with time-lapse photographing, it was revealed that VCFs provides cardiomyocytes with high migratory ability, and it was suggested that the provision of high migratory ability takes part in formation of a high level myocardial network in a myocardial tissue.

As a result of flow cytometry, it was revealed that localization of cardiomyocytes and fibroblasts in a created VCFs-compounded myocardial sheet was greatly different from a biological heart, and it was revealed that fibroblasts which express Platelet Endothelial Cell Adhesion Molecule-1 (PECAM-1, CD31) other than VCFs are localized in a heart.

INDUSTRIAL APPLICABILITY

By culturing using the cardiac cell culture materials of the present invention, functional cardiac tissues are preferably constructed. The cardiac cells obtained by the culture can be used as regenerative medicines such as transplantation, or as artificial organ materials such as cardiac tissue models.

While the invention has been described in detail and with reference to specific embodiments thereof, it will be apparent to one skilled in the art that various changes and modifications can be made therein without departing from the spirit and scope thereof.

The invention claimed is:

1. A method of enhancing growth of a cardiac cell, enhancing migration of a cardiac cell, and/or constructing a cardiac tissue, the method comprising:
increasing a number of fibroblasts expressing VCAM-1 or a gene encoding VCAM-1 in a fibroblast cell population; and contacting the cardiac cell or the cardiac tissue with the fibroblast cell population having the increased number of fibroblasts expressing VCAM-1 or a gene encoding VCAM-1 in a culture to culture the cardiac cell.

* * * * *